US009796662B2

(12) United States Patent
Allen et al.

(10) Patent No.: US 9,796,662 B2
(45) Date of Patent: Oct. 24, 2017

(54) ESTERAMINES AND DERIVATIVES FROM NATURAL OIL METATHESIS

(71) Applicant: Stepan Company, Northfield, IL (US)

(72) Inventors: Dave R Allen, Chicago, IL (US); Randal J Bernhardt, Antioch, IL (US); Aaron Brown, Chicago, IL (US); Anatoliy A Dameshek, Indian Creek, IL (US); Brian Holland, Deerfield, IL (US); Andrew D Malec, Irvine, CA (US); Ronald A Masters, Glenview, IL (US); Marshall J Nepras, Burlington, WI (US); Patti Skelton, Winder, GA (US); Laura Lee Whitlock, Highland Park, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 14/873,113

(22) Filed: Oct. 1, 2015

(65) Prior Publication Data

US 2016/0023989 A1    Jan. 28, 2016

Related U.S. Application Data

(62) Division of application No. 13/878,550, filed as application No. PCT/US2011/057596 on Oct. 25, 2011.
(Continued)

(51) Int. Cl.
| | |
|---|---|
| C07C 209/12 | (2006.01) |
| C07C 211/21 | (2006.01) |
| C07C 219/08 | (2006.01) |
| C07C 237/12 | (2006.01) |
| C07C 237/16 | (2006.01) |
| C07C 303/18 | (2006.01) |
| C07C 41/03 | (2006.01) |

(Continued)

(52) U.S. Cl.
CPC ............ *C07C 219/08* (2013.01); *A01N 25/02* (2013.01); *A01N 25/04* (2013.01); *A01N 25/30* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61K 8/92* (2013.01); *A61K 8/922* (2013.01); *A61Q 5/02* (2013.01); *A61Q 5/12* (2013.01); *A61Q 19/10* (2013.01); *A62D 1/0071* (2013.01); *B01F 17/0028* (2013.01); *B01F 17/0057* (2013.01); *C07C 6/04* (2013.01); *C07C 41/03* (2013.01); *C07C 43/11* (2013.01); *C07C 67/26* (2013.01); *C07C 69/533* (2013.01); *C07C 69/593* (2013.01); *C07C 209/12* (2013.01); *C07C 211/21* (2013.01); *C07C 231/12* (2013.01); *C07C 237/18* (2013.01); *C07C 303/18* (2013.01); *C08G 65/2615* (2013.01); *C08K 5/01* (2013.01); *C08K 5/20* (2013.01); *C09K 15/28* (2013.01); *C11C 3/00* (2013.01); *C11C 3/08* (2013.01); *C11D 1/002* (2013.01); *C11D 1/04* (2013.01); *C11D 1/28* (2013.01); *C11D 1/62* (2013.01); *C11D 1/652* (2013.01); *C11D 1/74* (2013.01); *C11D 1/83* (2013.01); *C11D 1/90* (2013.01); *C11D 1/92* (2013.01); *C11D 1/94* (2013.01); *C11D 3/48* (2013.01); *A61K 2800/805* (2013.01); *C09K 8/00* (2013.01)

(58) Field of Classification Search
None
See application file for complete search history.

(56) References Cited

U.S. PATENT DOCUMENTS

| | | |
|---|---|---|
| 2,653,970 A | 9/1953 | Fessler et al. |
| 2,990,403 A | 6/1961 | Gehshan et al. |

(Continued)

FOREIGN PATENT DOCUMENTS

| | | |
|---|---|---|
| CN | 101280515 A | 8/2007 |
| CS | 276206 | 4/1992 |

(Continued)

OTHER PUBLICATIONS

CAS No. 50278-96-1 (Entered STN Nov. 16, 1984).*
(Continued)

*Primary Examiner* — Paul A Zucker
*Assistant Examiner* — Mark Luderer
(74) *Attorney, Agent, or Firm* — Dilworth IP LLC

(57) ABSTRACT

Esteramine compositions and their derivatives are disclosed. The esteramines comprise a reaction product of a metathesis-derived $C_{10}$-$C_{17}$ monounsaturated acid, octadecene-1,18-dioic acid, or their ester derivatives with a tertiary alkanolamine. Derivatives made by quaternizing, sulfonating, alkoxylating, sulfating, and/or sulfitating the esteramines are also disclosed. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. The esteramines and derivatives are valuable for a wide variety of end uses, including cleaners, fabric treatment, hair conditioning, personal care (liquid cleansing products, conditioning bars, oral care products), antimicrobial compositions, agricultural uses, and oil field applications.

5 Claims, No Drawings

Related U.S. Application Data

(60) Provisional application No. 61/406,570, filed on Oct. 25, 2010, provisional application No. 61/406,556, filed on Oct. 25, 2010, provisional application No. 61/406,547, filed on Oct. 25, 2010.

(51) Int. Cl.

| | | |
|---|---|---|
| *C07C 43/11* | (2006.01) | |
| *C07C 6/04* | (2006.01) | |
| *C07C 67/26* | (2006.01) | |
| *C07C 69/533* | (2006.01) | |
| *C07C 69/593* | (2006.01) | |
| *A01N 25/02* | (2006.01) | |
| *A01N 25/04* | (2006.01) | |
| *A01N 25/30* | (2006.01) | |
| *A01N 33/12* | (2006.01) | |
| *A01N 37/18* | (2006.01) | |
| *A01N 37/44* | (2006.01) | |
| *A01N 41/04* | (2006.01) | |
| *A61K 8/41* | (2006.01) | |
| *A61K 8/42* | (2006.01) | |
| *A61K 8/44* | (2006.01) | |
| *A61K 8/46* | (2006.01) | |
| *A61K 8/92* | (2006.01) | |
| *A61Q 5/12* | (2006.01) | |
| *A61Q 19/10* | (2006.01) | |
| *A62D 1/02* | (2006.01) | |
| *B01F 17/00* | (2006.01) | |
| *C07C 231/12* | (2006.01) | |
| *C07C 237/18* | (2006.01) | |
| *C08G 65/26* | (2006.01) | |
| *C08K 5/01* | (2006.01) | |
| *C08K 5/20* | (2006.01) | |
| *C09K 15/28* | (2006.01) | |
| *C11C 3/00* | (2006.01) | |
| *C11C 3/08* | (2006.01) | |
| *C11D 1/00* | (2006.01) | |
| *C11D 1/04* | (2006.01) | |
| *C11D 1/28* | (2006.01) | |
| *C11D 1/62* | (2006.01) | |
| *C11D 1/65* | (2006.01) | |
| *C11D 1/74* | (2006.01) | |
| *C11D 1/83* | (2006.01) | |
| *C11D 1/90* | (2006.01) | |
| *C11D 1/92* | (2006.01) | |
| *C11D 1/94* | (2006.01) | |
| *C11D 3/48* | (2006.01) | |
| *A61Q 5/02* | (2006.01) | |
| *C09K 8/00* | (2006.01) | |

(56) References Cited

U.S. PATENT DOCUMENTS

| | | |
|---|---|---|
| 3,169,142 A | 2/1965 | Knaggs et al. |
| 3,544,613 A | 12/1970 | Knaggs et al. |
| 4,087,457 A | 5/1978 | Convers et al. |
| 4,148,821 A | 4/1979 | Nussbaum et al. |
| 4,275,013 A | 6/1981 | Tokosh et al. |
| 4,545,941 A | 10/1985 | Rosenburg |
| 4,692,441 A | 9/1987 | Alexander et al. |
| 5,415,737 A | 5/1995 | Phan et al. |
| 5,482,908 A | 1/1996 | Le-khac |
| 5,670,677 A | 9/1997 | Obiols et al. |
| 5,750,492 A | 5/1998 | Contet et al. |
| 5,783,534 A | 7/1998 | Wahle et al. |
| 5,939,059 A | 8/1999 | Franklin et al. |
| 5,964,907 A | 10/1999 | Farmer et al. |
| 6,004,913 A | 12/1999 | Iacobucci et al. |
| 6,004,923 A | 12/1999 | Oftring et al. |
| 6,420,330 B1 | 7/2002 | Stelter et al. |
| 6,737,392 B1 | 5/2004 | Keys et al. |
| 6,747,164 B2 | 6/2004 | Gustavsson et al. |
| 6,770,608 B2 | 8/2004 | Franklin et al. |
| 6,906,025 B2 | 6/2005 | Levinson |
| 6,914,146 B2 | 7/2005 | Queralt et al. |
| 7,163,056 B2 | 1/2007 | Cassidy et al. |
| 7,163,956 B2 | 1/2007 | Wilson et al. |
| 7,576,227 B2 | 8/2009 | Lysenko et al. |
| 7,960,599 B2 | 6/2011 | Millis et al. |
| 8,067,610 B2 | 11/2011 | Schrodi |
| 9,187,711 B2 * | 11/2015 | Allen .............. C07C 6/04 |
| 2001/0036909 A1 | 11/2001 | Levinson et al. |
| 2002/0064510 A1 | 5/2002 | Dalrymple et al. |
| 2007/0015928 A1 | 1/2007 | Zhang et al. |
| 2007/0154546 A1 | 7/2007 | Zhang et al. |
| 2008/0033026 A1 | 2/2008 | Zullo et al. |
| 2008/0139443 A1 | 6/2008 | Buzinski et al. |
| 2008/0255009 A1 | 10/2008 | Knox |
| 2009/0264672 A1 | 10/2009 | Abraham et al. |
| 2009/0305896 A1 | 12/2009 | Sun et al. |
| 2010/0016163 A1 | 1/2010 | Keiper et al. |
| 2010/0047499 A1 | 2/2010 | Braksmayer et al. |
| 2010/0145086 A1 | 6/2010 | Schrodi et al. |
| 2010/0282467 A1 | 11/2010 | Hutchison et al. |
| 2011/0113679 A1 | 5/2011 | Cohen et al. |
| 2011/0313180 A1 | 12/2011 | Uptain et al. |
| 2012/0071676 A1 | 3/2012 | Schrodi |
| 2012/0197031 A1 | 8/2012 | Firth et al. |
| 2013/0035502 A1 | 2/2013 | Cohen et al. |
| 2013/0035532 A1 | 2/2013 | Schrodi |

FOREIGN PATENT DOCUMENTS

| | | |
|---|---|---|
| EP | 0206947 | * 12/1986 |
| WO | WO-2008046106 | 4/2008 |
| WO | WO-2008048522 | 4/2008 |

OTHER PUBLICATIONS

Tundo et al., "Functionally Polymerized Surfactant Vesicles. Synthesis and Characterization," J. Am. Chem. Soc. 104(2), 1982, 456-461.*
Tetrahedron 68 2012, 1117.
Appl. Catal.A. 346 2009, 158.
J.C. Mol., Topics in Catalysis 27 2004, 97.
J. C. Mol., Green Chem., Apr. 2002, 5.
CAS No. 50278-96-1, entered in STN Database Nov. 16, 1984.
International Search Report and Written Opinion mailed in PCT/US11/57596 dated Mar. 14, 2012.
Exended European Search Report mailed in EP 11838498.1 dated Jul. 15, 2015.
http://www.hmdb.ca/metabolites/HMDB13206 (creation date: Nov. 30, 2009).
http://www.hmdb.ca/metabolites/HMDB13208 (creation date: Nov. 30, 2009).
Canadian Office Action dated Nov. 1, 2016 issued by the Canadian Intellectual Property Office, 4 pages.

* cited by examiner

ESTERAMINES AND DERIVATIVES FROM NATURAL OIL METATHESIS

This application is a division of U.S. application Ser. No. 13/878,550, filed May 15, 2013, now allowed, which is a national stage filing under 35 U.S.C. §371 of PCT/US2011/057596, filed Oct. 25, 2011, which claims the benefit of U.S. provisional applications 61/406,570, 61/406,556, and 61/406,547, all filed Oct. 25, 2010.

FIELD OF THE INVENTION

The invention relates to esteramine and derivative compositions that originate from renewable resources, particularly natural oils and their metathesis products.

BACKGROUND OF THE INVENTION

"Esteramines" are typically ester reaction products of fatty acids, fatty esters, or triglycerides and a tertiary alkanolamine (e.g., triethanolamine or N,N-dimethylethanolamine). While esteramines have value in and of themselves, they are more commonly quaternized to make "ester quats," cationic surfactants that have utility in a wide range of end-use applications, including fabric softening (see U.S. Pat. Nos. 5,670,677; 5,750,492; 6,004,913; 6,737,392; and U.S. Pat. Appl. Publ. No. 2001/0036909), cosmetics (U.S. Pat. No. 6,914,146), hair conditioning (U.S. Pat. No. 5,939,059), detergent additives for fuel (U.S. Pat. No. 5,964,907), antimicrobial compositions (U.S. Pat. No. 6,420,330), agricultural dispersants (U.S. Pat. Appl. Publ. No. 2010/0016163), and enhanced oil recovery (U.S. Pat. No. 7,163,056).

The fatty acids or esters used to make esteramines and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, *Green Chem.* 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, esteramines and their derivatives made from these feedstocks appear to be unknown. Moreover, esteramines and their derivatives have not been made from the $C_{18}$ unsaturated diesters that can be made readily by self-metathesis of a natural oil.

In sum, traditional sources of fatty acids and esters used for making esteramines and their derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants). New $C_{18}$ difunctional esteramines and derivatives are also potentially available from natural oil self-metathesis or $C_{10}$ unsaturated acid or ester self-metathesis. In addition to an expanded variety of precursors, the unsaturation present in the precursors allows for further functionalization, e.g., by sulfonation or sulfitation.

SUMMARY OF THE INVENTION

In one aspect, the invention relates to esteramine compositions. The esteramines comprise a reaction product of a metathesis-derived $C_{10}$-$C_{17}$ monounsaturated acid, octadecene-1,18-dioic acid, or their ester derivatives with a tertiary alkanolamine. The invention includes derivatives made by quaternizing, sulfonating, alkoxylating, sulfating, and/or sulfitating the esteramines. In one aspect, the ester derivative of the $C_{10}$-$C_{17}$ monounsaturated acid or octadecene-1,18-dioic acid is a lower alkyl ester. In other aspects, the ester derivative is a modified triglyceride made by self-metathesis of a natural oil or an unsaturated triglyceride made by cross-metathesis of a natural oil with an olefin. Esteramines and their derivatives are valuable for a wide variety of end uses, including cleaners, fabric treatment, hair conditioning, personal care (liquid cleansing products, conditioning bars, oral care products), antimicrobial compositions, agricultural uses, and oil field applications.

DETAILED DESCRIPTION OF THE INVENTION

In one aspect, the invention relates to esteramine compositions that comprise reaction products of a metathesis-derived $C_{10}$-$C_{17}$ monounsaturated acid, octadecene-1,18-dioic acid, or their ester derivatives with a tertiary alkanolamine.

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived esteramines and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to esteramine compositions made from them, including, for example, modified physical form, melting range, compactability, and other important properties. These differences should allow formulators that use esteramines and ester quats greater latitude or expanded choice as they use the esteramines in cleaners, fabric treatment, personal care, agricultural uses, and other end uses.

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized and then transesterified, the alkyl ester mixture will include a $C_{18}$ unsaturated diester. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making the inventive esteramine compositions.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive esteramine compositions.

An alternative to using a natural oil as a feedstock to generate the $C_{10}$-$C_{17}$ monounsaturated acid, octadecene-1,18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like.

Suitable alkylidene catalysts have the general structure:

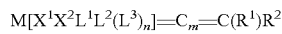

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

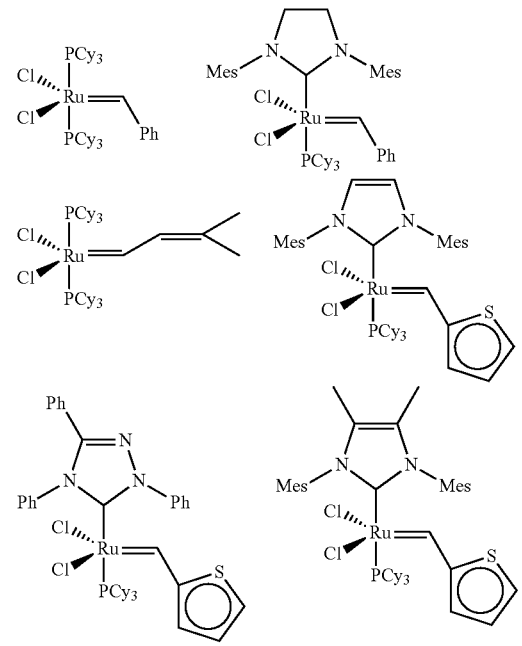

Heterogeneous catalysts suitable for use in the self- or cross-metathesis reaction include certain rhenium and molybdenum compounds as described, e.g., by J. C. Mol in Green Chem. 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The esteramines are made by reacting a metathesis-derived $C_{10}$-$C_{17}$ monounsaturated acid, octadecene-1,18-dioic acid, or their ester derivatives with a tertiary alkanolamine.

In one aspect, the ester derivative is a lower alkyl ester, especially a methyl ester. The lower alkyl esters are preferably generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be used "as is" to make an inventive esteramine mixture or it can be purified to isolate particular alkyl esters prior to making esteramines.

In another aspect, the ester derivative to be reacted with the tertiary alkanolamine is the metathesis-derived triglyceride discussed in the preceding paragraph. Instead of transesterifying the metathesis-derived triglyceride with a lower alkanol to generate lower alkyl esters as described above, the metathesis-derived triglyceride, following olefin stripping, is reacted directly with the tertiary alkanolamine to make an inventive esteramine mixture.

The skilled person will appreciate that "ester derivative" here encompasses other acyl equivalents, such as acid chlorides, acid anhydrides, or the like, in addition to the lower alkyl esters and glyceryl esters discussed above.

Suitable tertiary alkanolamines have a tertiary amine group and from one to three primary or secondary hydroxyl groups. In preferred alkanolamines, the tertiary nitrogen is attached to zero, one, or two $C_1$-$C_{10}$ alkyl groups, preferably $C_1$-$C_4$ alkyl groups, and from one to three hydroxyalkyl groups having from 2 to 4 carbons each, where the total number of alkyl and hydroxyalkyl groups is three. Suitable alkanolamines are well known and commercially available from BASF, Dow Chemical and other suppliers. They include, for example, triethanolamine, N-methyldiethanolamine, N,N-dimethylethanolamine, N,N-dimethylpropanolamine, N,N-dimethylisopropanolamine, N-methyldiisopropanolamine, N,N-diethylethanolamine, triisopropanolamine, and the like, and mixtures thereof. Particularly preferred alkanolamines are triethanolamine, N-methyldiethanolamine, and N,N-dimethylethanolamine, which are economical and readily available.

Suitable alkanolamines include alkoxylated derivatives of the compounds described above. Thus, for example, the alkanolamine used to make the esteramine can be a reaction product of an alkanolamine with 0.1 to 20 moles of ethylene oxide or propylene oxide per mole of —OH groups in the alkanolamine.

The esteramines are made using a well-known process that provides a unique product mixture because of the unconventional starting mixture of acid or ester derivatives. The reactants are typically heated, with or without a catalyst under conditions effective to esterify or transesterify the starting acid or ester with the tertiary alkanolamine. The reaction temperature is typically within the range of 80° C. to 300° C., preferably from 150° C. to 200° C., and more preferably from 165° C. to 180° C.

The relative amounts of alkanolamine and ester or acid reactants used depend on the desired stoichiometry and is left to the skilled person's discretion. Preferably, however, the equivalent ratio of acyl groups (in the metathesis-derived acid or ester derivative) to hydroxyl groups (in the tertiary alkanolamine) is within the range of 0.1 to 3, preferably from 0.3 to 1. As the examples below illustrate, the ratio is frequently about 1 (see the preparation of C10-2 or C10-4), but lower acyl:hydroxyl equivalent ratios are also common (see, e.g., the preparation of C10-6, acyl:OH=0.56).

Some esteramines have the formula:

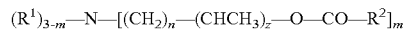

wherein:
$R^1$ is $C_1$-$C_6$ alkyl; $R^2$ is —$C_9H_{16}$—$R^3$ or —$C_{16}H_{30}$—$CO_2R^4$; $R^3$ is hydrogen or $C_1$-$C_7$ alkyl; $R^4$ is substituted or unsubstituted alkyl, aryl, alkenyl, oxyalkylene, polyoxyalkylene, glyceryl ester, or a mono- or divalent cation; m=1-3; n=1-4; z=0 or 1; and when z=0, n=2-4.

Preferably, $R^2$ is —$(CH_2)_7$—CH=$CHR^3$ or —$(CH_2)_7$—CH=CH—$(CH_2)_7$—$CO_2R^4$.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Some specific examples of $C_{10}$, $C_{12}$, $C_{14}$, and $C_{16}$-based esteramines appear below:

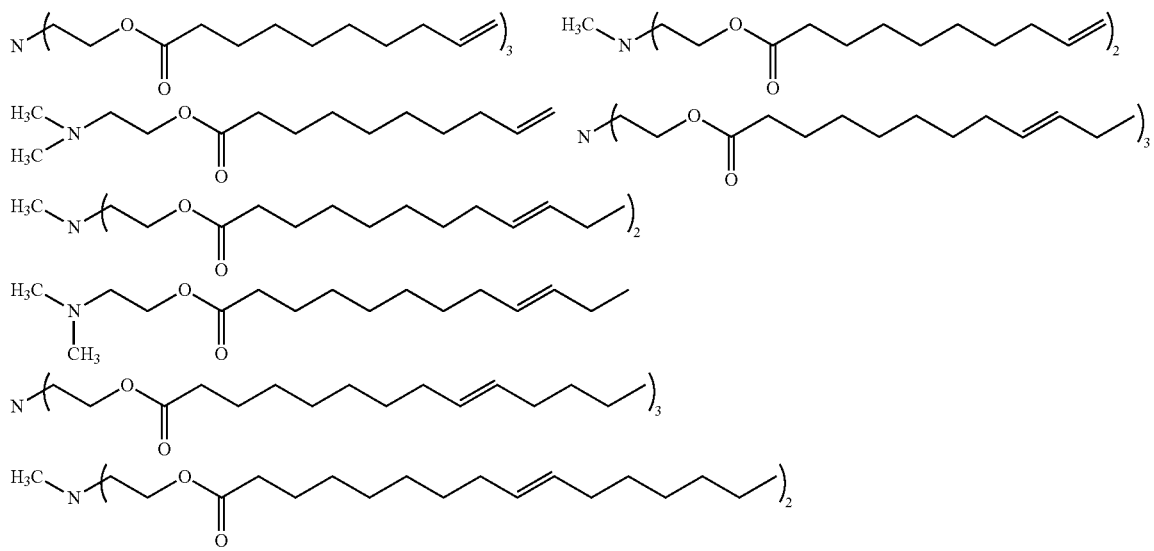

Some specific examples of $C_{18}$-based esteramines:

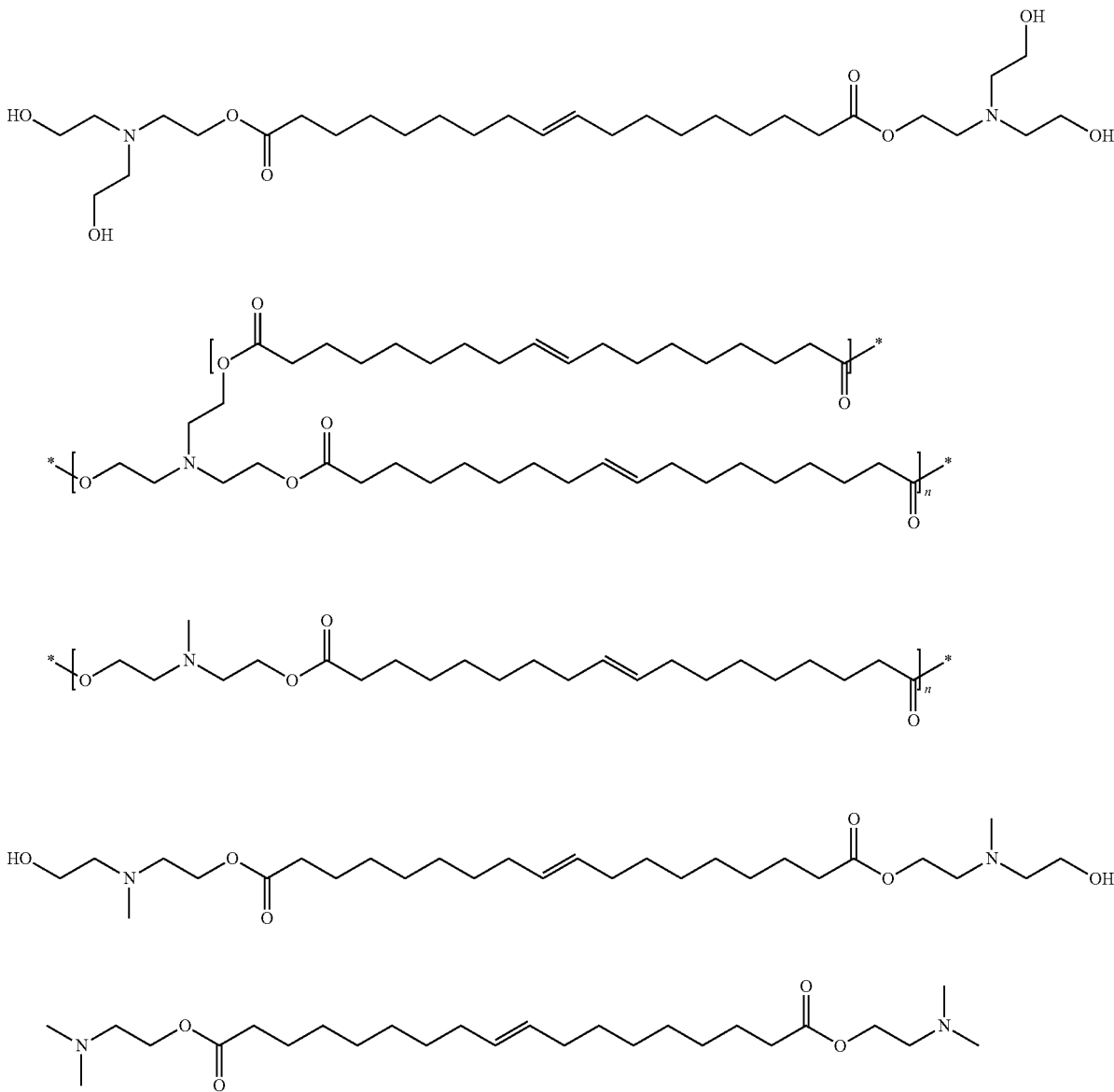

The esteramine product mixture can be complex when the ester derivative reacted with the alkanolamine is a modified triglyceride made by self-metathesis of a natural oil and separation to remove olefins (see, e.g., the MTG and PMTG products described below) or an unsaturated triglyceride made by cross-metathesis of a natural oil and an olefin and separation to remove olefins (see, e.g., the UTG and PUTG products described below). As is evident from the reaction schemes, the MTG and PMTG products include an unsaturated $C_{18}$ diesteramine as a principal component, while the UTG and PUTG products include a $C_{10}$ unsaturated esteramine component and one or more $C_{11}$ to $C_{17}$ unsaturated esteramine components. (For example, with 1-butene as the cross-metathesis reactant, as illustrated, a $C_{12}$ unsaturated esteramine component results.) Other components of the product mixtures are glycerin and saturated or unsaturated mono-, di-, or triesters that incorporate the alkanolamine. Despite the complexity, purification to isolate a particular species is often neither economical nor desirable for good performance.

Thus, in one aspect, the esteramine is produced by reacting an alkanolamine with a modified triglyceride made by self-metathesis of a natural oil. Self-metathesis of the natural oil provides a mixture of olefins and a modified triglyceride that is enriched in a $C_{18}$ unsaturated diester component along with $C_{16}$-$C_{18}$ saturated diesters. The olefins are stripped out, usually with heat and reduced pressure. When the self-metathesis product is reacted directly with the alkanolamine, a complex mixture results in which hydroxyl groups of the alkanolamine completely or partially displace glycerin from the glyceryl esters to form esteramine functionalities. Representative esteramine products below are made by reacting alkanolamines with MTG-0 (modified triglyceride from soybean oil) or PMTG-0 (modified triglyceride from palm oil). One example is the MTG 2:1 TEA ester:

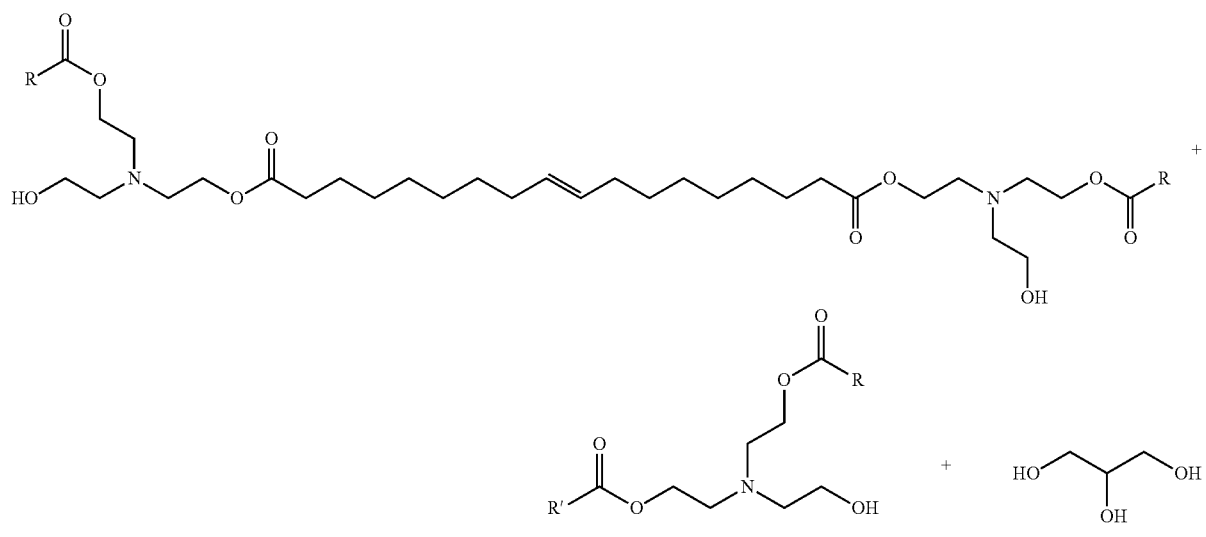

R = C16-C18 Sat. and Unsat.

In another aspect, the esteramine is produced by reacting an alkanolamine with an unsaturated triglyceride made by cross-metathesis of a natural oil with an olefin. Cross-metathesis of the natural oil and olefin provides a mixture of olefins and an unsaturated triglyceride that is rich in $C_{10}$ and $C_{12}$ unsaturated esters as well as $C_{16}$-$C_{18}$ saturated esters. The olefins are stripped out, usually with heat and reduced pressure. When the cross-metathesis product is reacted with the alkanolamine, a complex mixture results in which hydroxyl groups of the alkanolamine completely or partially displace glycerin from the glyceryl esters to form esteramine functionalities. Representative esteramine products below are made by reacting alkanolamines with UTG-0 (unsaturated triglyceride from cross-metathesis of soybean oil and 1-butene) or PUTG-0 (unsaturated triglyceride from cross-metathesis of palm oil with 1-butene). One example is the PUTG 2:1 TEA ester product:

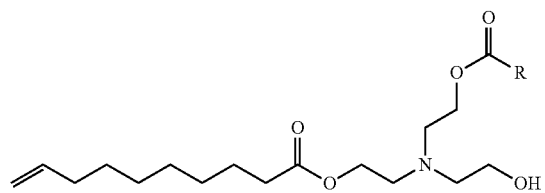

-continued

R' = C16, C18 Sat. + Unsat.

R = C10, C12-C18 Sat. and Unsat.

The reaction to form the esteramines can be performed under a nitrogen sparge or under vacuum to remove liberated alcohol. When glyceride esters are reactants, the liberated glycerin need not be removed from the product. The reaction is considered complete when the residual glyceride content of the product reaches the desired level.

The invention includes derivatives made by one or more of quaternizing, sulfonating, alkoxylating, sulfating, and sulfitating the esteramine. Methods for quaternizing tertiary amines are well known in the art. Quaternization of the esteramines is accomplished by warming them with a quaternizing agent such as an alkyl halide or dialkyl sulfate. Specific examples include dimethylsulfate, methyl chloride, epichlorohydrin, benzyl chloride, alkali metal chloroacetates, and the like. Dimethyl sulfate is particularly preferred. The reaction is generally performed at a temperature within the range of 30° C. to 150° C., preferably from 65° C. to 100° C., or more preferably from 80° C. to 90° C. The amount of quaternizing agent used is typically 0.8 to 1.0 mole equivalents based on the tertiary nitrogen content. The reaction is deemed complete when the free amine value is in the desired range as determined by perchloric acid titration. Suitable methods for quaternizing the esteramines are disclosed in U.S. Pat. Nos. 5,750,492; 5,783,534; 5,939,059; and 6,004,913, the teachings of which are incorporated herein by reference.

Examples of suitable $C_{10}$, $C_{12}$, $C_{14}$, and $C_{16}$-based quaternized esteramines ("ester quats"):
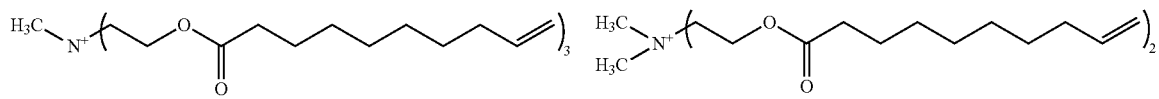
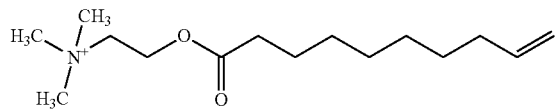
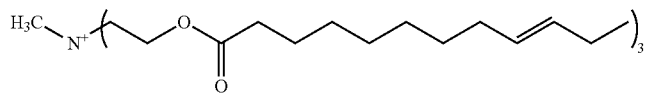
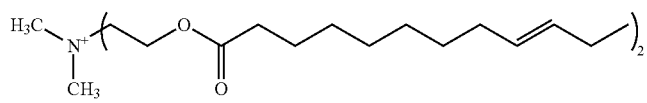
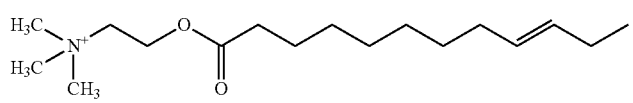
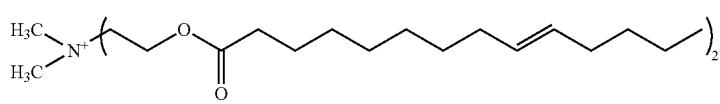
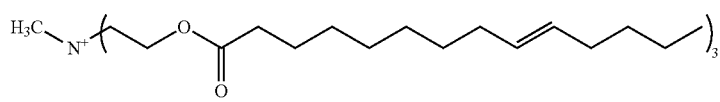
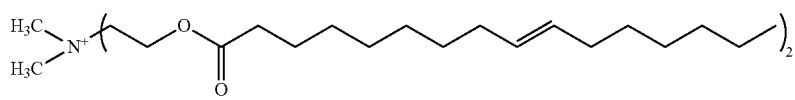
Examples of suitable $C_{18}$-based ester quats:
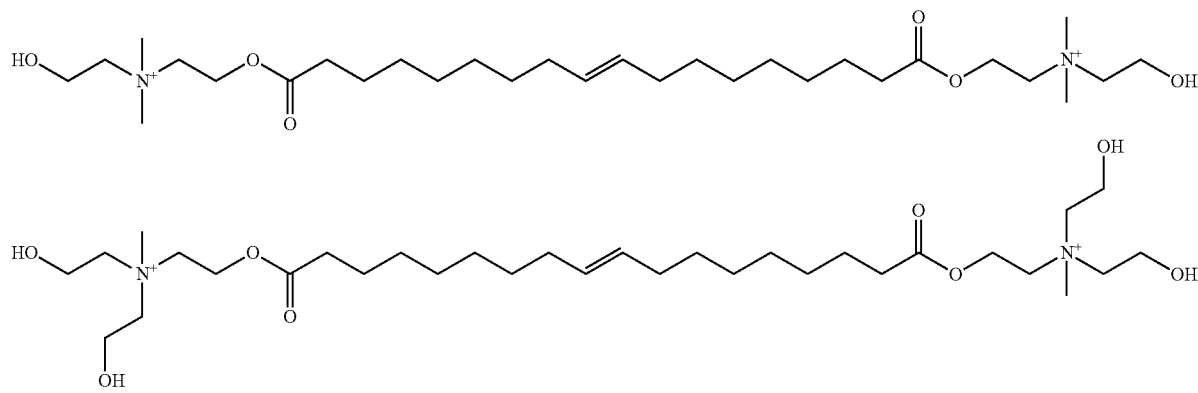

An exemplary ester quat based on a PUTG-based esteramine mixture:

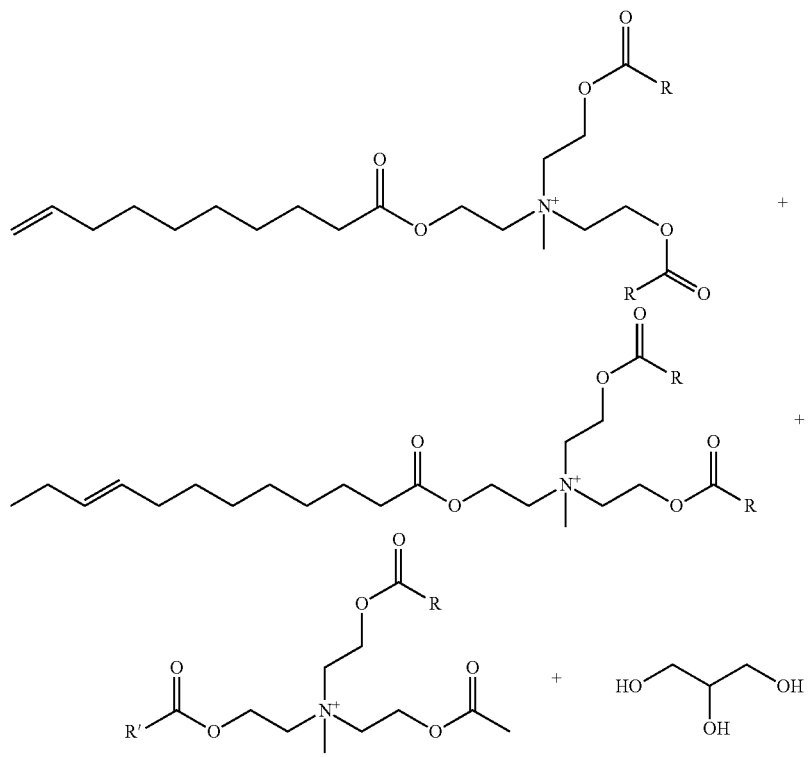

R' = C16, C18 Sat. + Unsat.
R = C10, C12-C18 Sat. and Unsat.

The esteramines and ester quats have unsaturation that can be sulfonated or sulfitated if desired. Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Sulfitation is accomplished by combining an olefin in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

When the esteramine has hydroxyl functionality, it can also be alkoxylated, sulfated, or both using well-known techniques. For instance, a hydroxyl-terminated esteramine can be alkoxylated by reacting it with ethylene oxide, propylene oxide, or a combination thereof to produce an alkoxylated alcohol. Alkoxylations are usually catalyzed by a base (e.g., KOH), but other catalysts such as double metal cyanide complexes (see U.S. Pat. No. 5,482,908) can also be used. The oxyalkylene units can be incorporated randomly or in blocks. The hydroxyl-functional esteramine can be sulfated, with or without a prior alkoxylation, and neutralized to give an alcohol sulfate according to known methods (see, e.g., U.S. Pat. No. 3,544,613, the teachings of which are incorporated herein by reference).

The esteramines and their quaternized, sulfonated, alkoxylated, sulfated, and sulfitated derivatives can be incorporated into many compositions for use as, for example, surfactants, emulsifiers, skin-feel agents, film formers, rheological modifiers, biocides, biocide potentiators, solvents, release agents, and conditioners. The compositions find value in diverse end uses, such as personal care (liquid cleansing products, conditioning bars, oral care products), household products (liquid and powdered laundry detergents, liquid and sheet fabric softeners, hard and soft surface cleaners, sanitizers and disinfectants), and industrial or institutional cleaners.

The esteramines and derivatives can be used in emulsion polymerizations, including processes for the manufacture of latex. They can be used as surfactants, wetters, dispersants, or solvents in agricultural applications, as inert ingredients in pesticides, or as adjuvants for delivery of pesticides for crop protection, home and garden, and professional applications. The esteramines and derivatives can also be used in oil field applications, including oil and gas transport, production, stimulation and drilling chemicals, reservoir conformance and enhancement uses, and specialty foamers. The compositions are also valuable as foam moderators or dispersants for the manufacture of gypsum, cement wall board, concrete additives and firefighting foams. The compositions are used as coalescents for paints and coatings, and as polyurethane-based adhesives.

In food and beverage processing, the esteramines and derivatives can be used to lubricate the conveyor systems used to fill containers. When combined with hydrogen peroxide, the esteramines and derivatives can function as low foaming disinfectants and sanitization agents, odor reducers, and as antimicrobial agents for cleaning and protecting food or beverage processing equipment. In industrial, institutional and laundry applications, the esteramines and derivatives, or their combination with hydrogen peroxide, can be used to remove soil and sanitize and disinfect fabrics and as antimicrobial film-forming compositions on hard surfaces.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

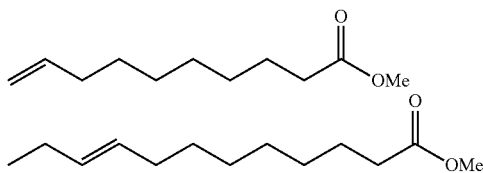

The procedures of U.S. Pat. Appl. Publ. No. 2011/0113679, the teachings of which are incorporated herein by reference, are used to generate feedstocks C10-0 and C12-0 as follows:

Example 1A: Cross-Metathesis of Soybean Oil and 1-Butene. A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium (3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America; 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B. The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C. The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D. The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E. Separation of Olefins from Modified Triglyceride. A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 µtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F. Methanolysis of Modified Triglyceride. A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G. Isolation of Methyl Ester Feedstocks. A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Preparation of Fatty Acids from Methyl Esters

Methyl esters C10-0, C12-0, and Mix-0 are converted to their respective fatty acids (C10-36, C12-39, and Mix-67) as follows.

Potassium hydroxide/glycerin solution (16-17 wt. % KOH) is added to a flask equipped with an overhead stirrer, thermocouple, and nitrogen sparge, and the solution is heated to ~100° C. The methyl ester is then added to the KOH/glycerine solution. An excess of KOH (2-4 moles KOH per mole of methyl ester) is used; for monoesters the mole ratio is about 2, and for diesters about 4. The reaction temperature is raised to 140° C. and heating continues until gas chromatography analysis indicates complete conversion. Deionized water is added so that the weight ratio of reaction mixture to water is about 1.5. The solution is heated to 90° C. to melt any fatty acid salt that may have solidified. Sulfuric acid (30% solution) is added and mixed well to convert the salt to the free fatty acid, and the layers are allowed to separate. The aqueous layer is drained, and the fatty acid layer is washed with water until the aqueous washes are neutral. The crude fatty acids are used "as is" for making some of the esteramines.

Analysis of Unreacted Amines in Esteramines

Several grams of esteramine are dissolved in 100 mL of a 70/30 (vol/vol) mixture of toluene and isopropanol and this solution is extracted with one 50-mL portion and two 25-mL portions of 20% aqueous NaCl. The combined aqueous layers are then titrated with 0.1 N aqueous HCl. The amount of extracted amine is interpreted as being the amount of unreacted amine. It is calculated from the titration endpoint volume and the molecular weight of the starting amine used to prepare the esteramine composition.

C10-2: C10 TEA Ester

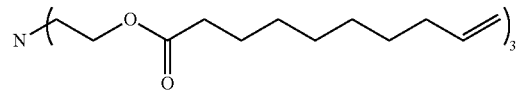

Fatty acid C10-36 (176.7 g, 0.984 mol), base catalyst, and triethanolamine (49.0 g, 0.328 mol) are charged to a 4-neck flask under a blanket of nitrogen. A subsurface sparge of nitrogen (200 mL/min) is maintained. The mixture is stirred (170 rpm) and heated without a vacuum to 185° C. and held for 21 h. Free fatty acid content is found by titration to be 0.078 meq/g. The reaction temperature is increased to 190° C. under vacuum (50 mm Hg) and heating continues for an additional 4 h. After cooling, the esteramine product, C10-2, has a fatty acid content of 0.0651 meq/g and an unreacted triethanolamine value of 0.77%.

C10-4: C10 MDEA Ester

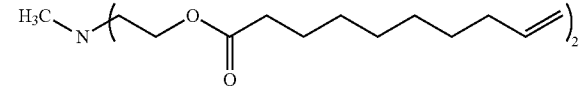

Fatty acid C10-36 (168.5 g, 0.939 mol), base catalyst, and N-methyldiethanolamine (55.9 g, 0.469 mol) are charged to a 4-neck flask under a blanket of nitrogen. A subsurface sparge of nitrogen (200 mL/min) is maintained. The mixture is stirred (170 rpm) and heated without a vacuum to 185° C. and held for 20 h. Free fatty acid content is found by titration: 0.133 meq/g. Reaction temperature is reduced to 180° C. (200 mm Hg) and heating continues for another 8 h. Fatty acid content: 0.123 meq/g. Additional N-methyldiethanolamine (7.2 g) is added, and heating continues at 180° C. (200 mm Hg) for another 3 h. After cooling, the esteramine product, C10-4, has a fatty acid content of 0.0649 meq/g and an unreacted N-methyldiethanolamine value of 1.11%.

C10-6: C10 DMEA Ester

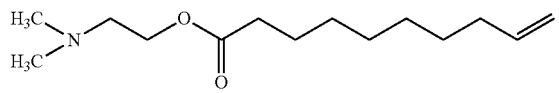 [SMILES: C=CCCCCCCCC(=O)OCCN(C)C]

Fatty acid C10-36 (153.7 g, 0.890 mol) and N,N-dimethylethanolamine (142.7 g, 1.60 mol) are charged to a flask equipped with heating mantle, temperature controller, mechanical agitator, nitrogen sparge, five-plate Oldershaw column, and condenser. The mixture is gradually heated to 180° C. while the overhead distillate temperature is kept below 105° C. After the reaction mixture temperature reaches 180° C., it is held at this temperature overnight. Free fatty acid content by $^1$H NMR: 5% (essentially complete). The mixture is cooled to 90° C. and the column, condenser, and nitrogen sparge are removed. Vacuum is applied in increments to 20 mm Hg over ~1 h, held at held at 20 mm Hg for 0.5 h, then improved to full vacuum for 1.5 h. The esteramine product, C10-6, has an unreacted dimethylethanolamine value of 0.41%. Purity is confirmed by a satisfactory $^1$H NMR spectrum.

C12-2: C12 TEA Ester

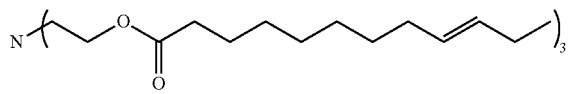

Methyl ester C12-0 (193.9 g, 0.912 mol), base catalyst, and triethanolamine (45.5 g, 0.305 mol) are charged to a 4-neck flask under a blanket of nitrogen. A subsurface sparge of nitrogen (200 mL/min) is maintained. The mixture is stirred (170 rpm) and heated without a vacuum to 165° C. and held for 16 h. $^1$H NMR indicates essentially complete reaction with a trace of unreacted methyl ester. After cooling, the esteramine product, C12-2, has an unreacted triethanolamine value of 0.06%.

C12-4: C12 MDEA Ester

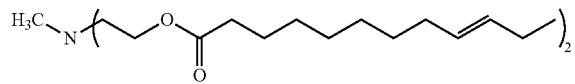

Methyl ester C12-0 (185.9 g, 0.875 mol), base catalyst, and N-methyldiethanolamine (54.9 g, 0.460 mol) are charged to a 4-neck flask under a blanket of nitrogen. A subsurface sparge of nitrogen (200 mL/min) is maintained. The mixture is stirred (170 rpm) and heated without a vacuum to 165° C. and held for 16 h. The temperature is increased to 170° C. (at 200 mm Hg) and heating continues for 3 h. After cooling, the esteramine product, C12-4, has an unreacted N-methyldiethanolamine value of 3.22%. Purity is confirmed by a satisfactory $^1$H NMR spectrum.

C12-6: C12 DMEA Ester

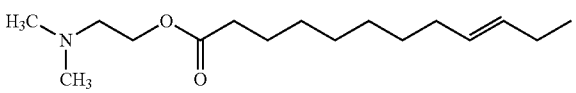

Fatty acid C12-39 (187.2 g, 0.917 mol) and N,N-dimethylethanolamine (147.1 g, 1.65 mol) are charged to a flask equipped with heating mantle, temperature controller, mechanical agitator, nitrogen sparge, five-plate Oldershaw column, and condenser. The mixture is gradually heated to 180° C. while the overhead distillate temperature is kept below 105° C. After the reaction mixture temperature reaches 180° C., it is held at this temperature overnight. Free fatty acid content: 1.59%. The mixture is cooled to 90° C. and the column, condenser, and nitrogen sparge are removed. After the usual vacuum stripping, the esteramine product, C12-6, has an unreacted dimethylethanolamine value of 0.084%. Purity is confirmed by a satisfactory $^1$H NMR spectrum.

Preparation of Methyl 9-Hexadecenoate ("C16-0") Feedstock

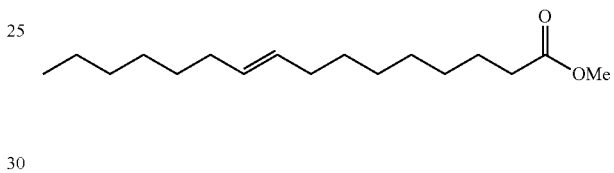

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

C16-3: C16 Fatty Acid

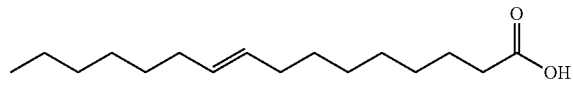 [SMILES: CCCCCC/C=C/CCCCCCCC(=O)O]

Potassium hydroxide (20 g) and glycerol (112 g) are added to a round-bottom flask equipped with a Dean-Stark trap. The mixture is stirred mechanically and heated to 100° C. under nitrogen until homogeneous. Unsaturated methyl ester C16-0 (80 g) is added and the mixture is heated to 120° C., then held for 3 h. Gas chromatography indicates a complete conversion to the desired acid. Deionized water (100 g) and 30% aq. sulfuric acid solution (132 g) are added to the reaction mixture. The layers are separated and the organic phase is washed with deionized water (3×220 mL) at 60° C. Short-path distillation is performed to remove water (100° C., full vacuum, 2 h). The product, C16-3, obtained in 92% yield, is analyzed: acid value: 219.7 mg KOH/g; moisture: 0.1%; isomer ratio: 18.8 cis-181.2 trans-. $^1$H NMR (DMSO), δ (ppm): 5.36 (CH═CH); 2.34 (—CH$_2$—C(O)—OH).

C16-6: C16 MDEA Ester

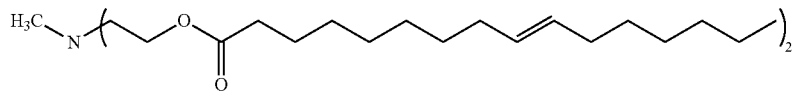

The procedure used to make C12-4 is generally followed using fatty methyl ester C16-0 (162.5 g) and N-methyldiethanolamine (35.7 g). The product, C16-6, has an unreacted N-methyldiethanolamine value of 0.88% and gives a satisfactory $^1$H NMR spectrum.

Ester Quat Formation from C10 and C12 Esteramines

Each of the esteramines prepared as described above is quaternized as follows. Table 2 summarizes the products, amount of dimethyl sulfate ("DMS," quaternizing agent), reaction time, temperature, and amount of isopropyl alcohol ("IPA") solvent. The amount of DMS used for all reactions is determined by perchloric acid titration ("PAT" value) of the esteramine.

The esteramine is charged to a round-bottom flask equipped with a reflux condenser, thermocouple/heating mantle, and nitrogen inlet. The sample is heated to 65° C. if IPA is used to help solubilize the esteramine; otherwise, it is heated to 75-80° C. DMS is added dropwise via an addition funnel. Temperature is kept at or below 70° C. if IPA is included and at or below 85° C. if it is not used. After the DMS is added, the temperature is increased to 70° C. (if IPA is included) and stirred for 2-3 h; otherwise, the temperature is raised to 85° C. and stirred for 1 h. The reaction is considered complete if the PAT value indicates <5% quaternizable amine remaining based on the original PAT value of the esteramine. IPA (~10 wt. %) is added (unless added previously) to help eliminate residual DMS. The reaction mixture is also heated at 80-85° C. for 1 h to ensure complete DMS removal; contents are also tested with a Dräger apparatus for residual DMS.

TABLE 2

C10 and C12 Ester Quat Synthesis

| Ester Quat Product | Esteramine (g) | DMS (g) | Time (h) | Rxn. Temp. (° C.) | % Quat by PAT Value | IPA (g) |
|---|---|---|---|---|---|---|
| C10-3: C10 TEA Ester Quat | 147.5 | 30.5 | 3 | 70 | 98.5 | 20.0 |
| C10-5: C10 MDEA Ester Quat | 148.9 | 46.5 | 1 | 85 | 98.7 | 22.0 |
| C10-7: C10 DMEA Ester Quat | 98.9 | 49.6 | 3 | 70 | 98.2 | 26.2 |
| C12-3: C12 TEA Ester Quat | 154.0 | 26.6 | 3 | 70 | 98.0 | 20.0 |
| C12-5: C12 MDEA Ester Quat | 162.4 | 38.6 | 1 | 85 | 98.4 | 23.0 |

TABLE 2-continued

C10 and C12 Ester Quat Synthesis

| Ester Quat Product | Esteramine (g) | DMS (g) | Time (h) | Rxn. Temp. (° C.) | % Quat by PAT Value | IPA (g) |
|---|---|---|---|---|---|---|
| 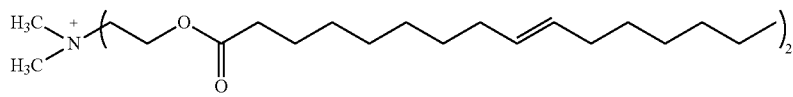<br>C12-7: C12 DMEA Ester Quat | 99.8 | 44.6 | 3 | 70 | 98.8 | 24.0 |

C16-7: C16 MDEA Ester Quat

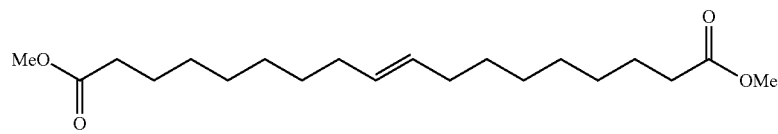 [SMILES: COC(=O)CCCCCCC/C=C/CCCCCCCC(=O)OC]

MDEA ester C16-6 (127.8 g) is placed in a round-bottom flask equipped with a condenser, thermocouple, heating mantle, and nitrogen inlet. The contents are heated to 80° C. Dimethyl sulfate (27.7 g) is added via addition funnel. The amount of DMS is added to achieve >95% quaternization as determined from the perchloric acid titration (PAT) value. After the DMS addition, the temperature is raised to 85° C. Two hours after the DMS addition is complete, the percent quaternization is ~97%. Isopropyl alcohol (17.0 g) is added and the temperature is kept at 85° C. After 1 h, the mixture is cooled to room temperature. The product, C16-7, is removed and tested with a Dräger apparatus for residual DMS.

Feedstock Synthesis

Preparation of Dimethyl 9-Octadecene-1,18-dioate ("Mix-0" or "C18-0"

Eight samples of methyl 9-dodecenoate (10.6 g each, see Table 3) are warmed to 50° C. and degassed with argon for 30 min. A metathesis catalyst ([1,3-bis-(2,4,6-trimethylphenyl)-2-imidazolidinylidene]dichlororuthenium (3-methyl-2-butenylidene)-(tricyclohexylphosphine), product of Materia) is added to the methyl 9-dodecenoate (amount indicated in Table 3) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 3. "Mix-0" is an 80:20 trans-/cis-isomer mixture obtained from the reaction mixture. Crystallization provides the all-trans-isomer feed, "C18-0."

TABLE 3

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

Esteramines are prepared from the C18 diesters, "Mix-0" or "Mix-0-2" (80:20 trans-/cis-mixtures) or "C18-0" (100% trans-) as described below.

MIX-3: C18 TEA Ester (2:1) Mix (80:20 Trans-/Cis-)

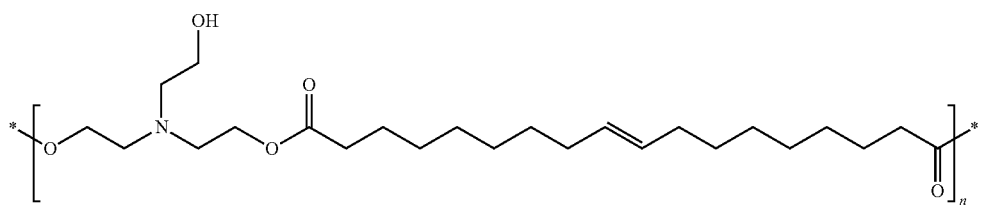

Methyl ester Mix-O-2 (246.0 g, 0.720 mol), base catalyst, and triethanolamine (107.4 g, 0.720 mol) are charged to a 4-neck flask equipped with a distillation head and condenser. The contents are heated to 80° C., then to 135° C., under a nitrogen flow (150 mL/min). Methanol distills as the reaction proceeds, and the temperature is gradually increased to 175° C. over 2 h. The nitrogen flow is then directed below the liquid surface. After 3.5 h at 175° C., the mixture is cooled. The methanol collected is 77.4% of the theoretical amount. The mixture has become viscous and the reaction is deemed complete. The esteramine product, Mix-3, has an unreacted triethanolamine value of 3.46%.

MIX-5: C18 TEA Ester (1:1) Mix (80:20 Trans-/Cis-)

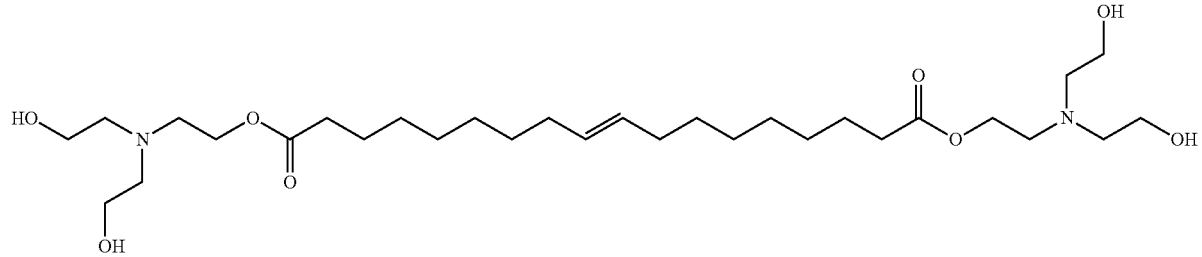 [SMILES: O=C(CCCCCCC/C=C/CCCCCCCC(=O)OCCN(CCO)CCO)OCCN(CCO)CCO]

Methyl ester Mix-0-2 (167.0 g, 0.489 mol), base catalyst, and triethanolamine (145.9 g, 0.978 mol) are charged to a 4-neck flask under a blanket of nitrogen. A subsurface sparge of nitrogen (200 mL/min) is maintained. The mixture is stirred (170 rpm) and heated without a vacuum to 150° C. and held for 1 h, after which the temperature is increased to 180° C. and held for 22 h. The temperature is reduced to 175° C. (400 mm Hg) for another 4 h. After cooling, the esteramine product, Mix-5, has an unreacted triethanolamine value of 14.6%.

MIX-7: C18 TEA Ester (3:1) Mix (80:20 Trans-/Cis-)

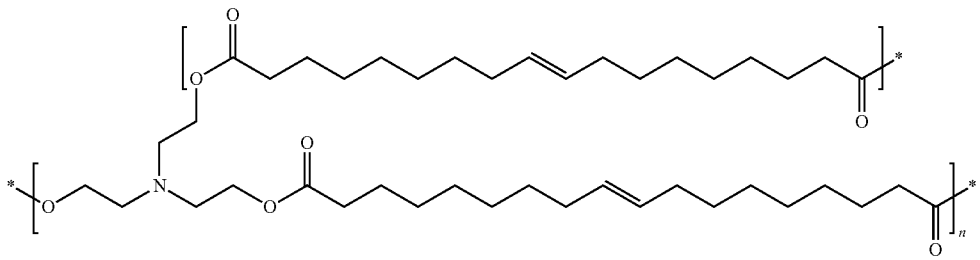

Methyl ester Mix-0-2 (293.0 g, 0.858 mol), base catalyst, and triethanolamine (85.3 g, 0.572 mol) are charged to a 4-neck flask equipped with a distillation head and condenser. The contents are heated to 130° C. under a nitrogen flow (150 mL/min). Methanol distills as the reaction proceeds, and the temperature is gradually increased to 175° C. over 2 h. The nitrogen flow is then directed below the liquid surface. After 2 h at 175° C., the mixture is cooled. The methanol collected is 62.0% of the theoretical amount. The mixture has become viscous and the reaction is deemed complete. The esteramine product, Mix-7, has an unreacted triethanolamine value of 0.99%.

C18-9: C18 MDEA Ester (2:1) Mix (100% Trans-)

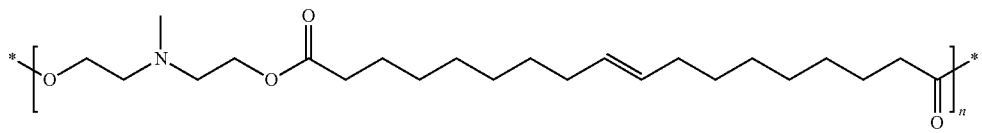

Methyl ester C18-0 (258.2 g, 0.758 mol), base catalyst, and N-methyldiethanolamine (90.4 g, 0.758 mol) are charged to a 4-neck flask under a blanket of nitrogen. A subsurface sparge of nitrogen (175 mL/min) is maintained. The mixture is stirred (170 rpm) and heated without a vacuum to 130° C. and held for 1 h, after which the temperature is increased to 150° C. and held for 3 h. Methanol evolves rapidly, then slows. Additional N-methyldiethanolamine (0.68 g) is added and heating continues at 170° C. (50 mm Hg) for 7 h, then at 180° C. (50 mm Hg) for another 7 h. Because $^1$H NMR analysis shows 35% of unreacted methyl ester content, heating continues at 180° C. (760 mm Hg) for another 70 h. NMR shows that the reaction is 93% complete. More N-methyldiethanolamine (5.5 g) is added, and the mixture is heated to 180° C. and held overnight. After cooling, the esteramine product, C18-9, has an unreacted N-methyldiethanolamine value of 0.53%.

MIX-9: C18 MDEA Ester (2:1) Mix (80:20 Trans-/Cis-)

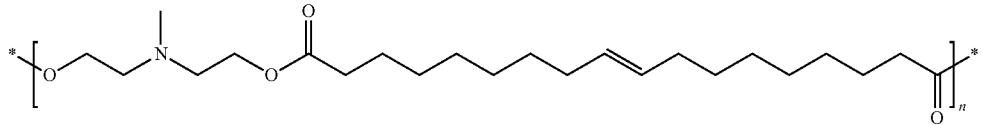

Methyl ester Mix-0-2 (266.0 g, 0.779 mol), base catalyst, and N-methyldiethanolamine (92.8 g, 0.779 mol) are charged to a 4-neck flask under a blanket of nitrogen. An above-surface sparge of nitrogen (50-75 mL/min) is maintained. The mixture is stirred (170 rpm) and heated without a vacuum to 130° C. and held for 6.75 h. The temperature is increased gradually over 9 h to 175° C. and held at 175° C. (400 mm Hg) for 4 h, then at 175° C. (760 mm Hg) for 20.5 h. After cooling, the esteramine product, Mix-9, has an unreacted N-methyldiethanolamine value of 1.25%.

MIX-11: C18 MDEA Ester (1:1) Mix (80:20 Trans-/cis-)

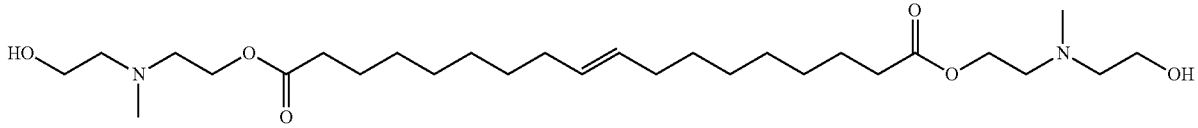 [SMILES: CN(CCO)CCOC(=O)CCCCCCC/C=C/CCCCCCCC(=O)OCCN(C)CCO]

Methyl ester Mix-0-2 (186.4 g, 0.546 mol), base catalyst, and N-methyldiethanolamine (130.0 g, 1.09 mol) are charged to a 4-neck flask under a blanket of nitrogen. An above-surface sparge of nitrogen (50-75 mL/min) is maintained. The mixture is stirred (170 rpm) and heated without a vacuum with a gradual temperature ramp as follows: to 130° C. and held for 4.75 h; to 140° C. and held for 16.5 h; to 150° C. and held for 6.5 h; to 160° C. and held for 18 h. Thereafter, heating continues at 170° C. for 8 h with a subsurface nitrogen sparge (50 to 75 mL/min). After cooling, the esteramine product, Mix-11, has an unreacted N-methyldiethanolamine value of 10.6%.

MIX-13: C18 MDEA Ester (3:1) Mix (80:20 Trans-/Cis-)

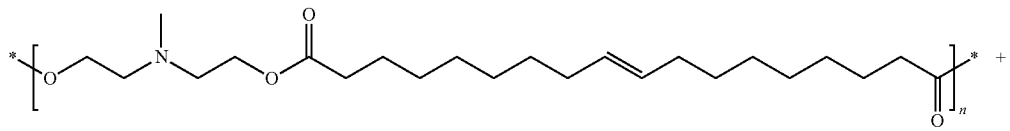

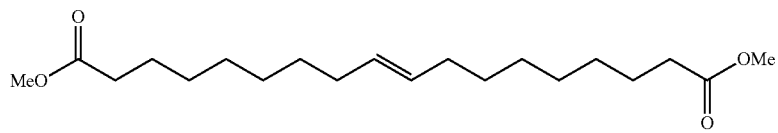

Methyl ester Mix-0-2 (311.0 g, 0.910 mol), base catalyst, and N-methyldiethanolamine (72.3 g, 0.607 mol) are charged to a 4-neck flask under a blanket of nitrogen. An above-surface sparge of nitrogen (50-75 mL/min) is maintained. The mixture is stirred (170 rpm) and heated, initially without a vacuum, with a gradual temperature ramp as follows: to 130° C. and held for 6.5 h; to 140° C. and held for 2 h; to 150° C. and held for 2 h; to 160° C. and held for 1 h; to 170° C. and held for 2.5 h; to 175° C. (400 mm Hg) and held for 2.5 h; to 175° C. (760 mm Hg) and held for 20.5 h; to 160° C. (760 mm Hg) and held for 16 h. After cooling, the esteramine product, Mix-13, has an unreacted N-methyldiethanolamine value of 0.45%.

MIX-67: C18 diFatty Acid (80:20 Trans-/cis-)

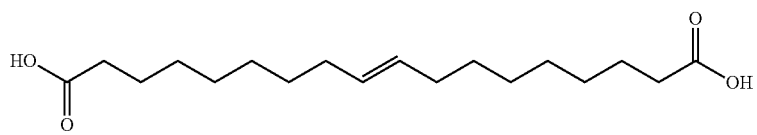 [SMILES: O=C(O)CCCCCCC/C=C/CCCCCCCC(=O)O]

MIX-15: C18 diDMEA Ester Mix (80:20 Trans-/Cis-)

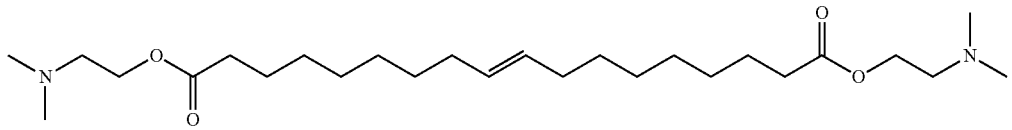

Fatty acid Mix-67 (170.7 g, 0.546 mol), prepared by hydrolysis of Mix-0, and N,N-dimethylethanolamine (175.3 g, 1.967 mol) are charged to a flask equipped with a heating mantle, temperature controller, mechanical agitator, nitrogen sparge, five-plate Oldershaw column, and condenser. The mixture is gradually heated to 145° C. while the overhead distillate temperature is kept below 105° C. The reaction temperature is held at 145-150° C. for 4 h, then increased over 2 h to 180° C., then held at 180° C. overnight. The free fatty acid content is 3.30%, and the reaction is deemed complete. The mixture is cooled to 90° C. and the product is vacuum stripped (20 mm Hg, 0.5 h, then full vacuum, 1.5 h). The esteramine, Mix-15, has an unreacted dimethylethanolamine value of 0.23% and gives a satisfactory $^1$H NMR spectrum.

Ester Quat Formation from C18 and MIX C18 Esteramines

Each of the esteramines prepared as described above is quaternized as follows. Table 4 summarizes the products, amount of dimethyl sulfate ("DMS," quaternizing agent), reaction time, temperature, and amount of isopropyl alcohol ("IPA") solvent. The amount of DMS used for all reactions is determined by perchloric acid titration ("PAT" value) of the esteramine.

The esteramine is charged to a round-bottom flask equipped with a reflux condenser, thermocouple/heating mantle, and nitrogen inlet. The sample is heated to 50-65° C. if IPA is used to help solubilize the esteramine; otherwise, it is heated to 75-80° C. DMS is added dropwise via an addition funnel. Temperature is kept at or below 70° C. if IPA is included and at or below 85° C. if it is not used. After the DMS is added, the temperature is increased to 70° C. (if IPA is included) and stirred for 2-3 h; otherwise, the temperature is raised to 85° C. and stirred for 1 h. The reaction is considered complete if the PAT value indicates <5% quaternizable amine remaining based on the original PAT value of the esteramine. IPA (10-50 wt. %) is added (unless added previously) to help eliminate residual DMS. The reaction mixture is also heated at 80-85° C. for 1-3 h to ensure complete DMS removal; contents are also tested with a Dräger apparatus for residual DMS.

TABLE 4

C18 and MIX C18 Ester Quat Synthesis

| Ester Quat Product | Esteramine (g) | DMS (g) | Time (h) | Rxn. Temp. (°C.) | % Quat by PAT Value | IPA (g) |
|---|---|---|---|---|---|---|
| MIX-4: C18 TEA Ester (2:1) Mix Quat | 156.7 | 43.4 | 3 | 70 | 97.6 | 50.0 |
| MIX-6: C18 TEA Ester (1:1) Mix Quat | 116.0 | 48.5 | 3 | 70 | 97.4 | 41.1 |
| MIX-8: C18 TEA Ester (3:1) Mix Quat | 181.3 | 36.5 | 3 | 70 | 98.0 | 72.5 |

TABLE 4-continued

C18 and MIX C18 Ester Quat Synthesis

| Ester Quat Product | Esteramine (g) | DMS (g) | Time (h) | Rxn. Temp. (° C.) | % Quat by PAT Value | IPA (g) |
|---|---|---|---|---|---|---|
| C18-10: C18 MDEA Ester (2:1) Mix Quat | 143.5 | 38.0 | 3 | 70 | 98.4 | 45.3 |
| MIX-10: C18 MDEA Ester (2:1) Mix Quat | 146.7 | 37.5 | 3 | 70 | 98.5 | 35.0 |
| MIX-12: C18 MDEA Ester (1:1) Mix Quat | 113.3 | 51.3 | 1 | 85 | 98.5 | 18.0 |
| MIX-14: C18 MDEA Ester (3:1) Mix Quat | 186.3 | 36.3 | 1 | 80 | 98.0 | 39.3 |

TABLE 4-continued

C18 and MIX C18 Ester Quat Synthesis

| Ester Quat Product | Esteramine (g) | DMS (g) | Time (h) | Rxn. Temp. (° C.) | % Quat by PAT Value | IPA (g) |
|---|---|---|---|---|---|---|
| MIX-16: C18 diMEA DiQuat | 91.8 | 46.6 | 2 | 70 | 97.8 | 30.0 |

Modified Triglyceride Based on Soybean Oil ("MTG-0")

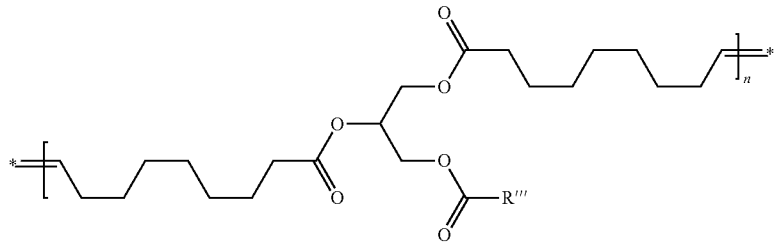

The procedures of Examples 1A and 1E are generally followed except that 1-butene is omitted.

Mod. Triglyceride from Cross-Metathesis of Soybean Oil and 1-Butene ("UTG-0")

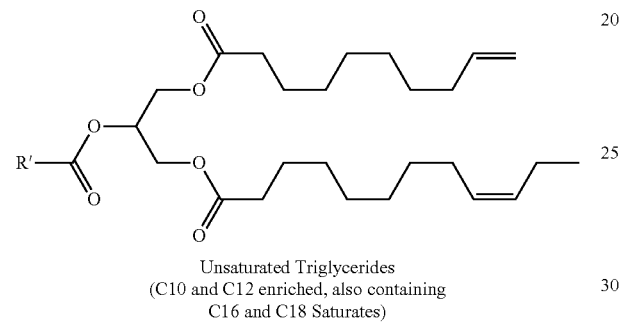

Unsaturated Triglycerides
(C10 and C12 enriched, also containing
C16 and C18 Saturates)

The procedures of Examples 1A and 1E are generally followed to produce UTG-0 from soybean oil and 1-butene.

Modified Triglyceride Based on Palm Oil ("PMTG-0")

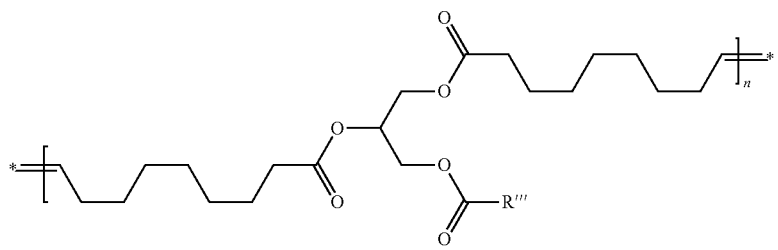

The procedure used to make MTG-0 is followed, except that palm oil is used instead of soybean oil.

Mod. Triglyceride from Cross-Metathesis of Palm Oil and 1-Butene ("PUTG-0")

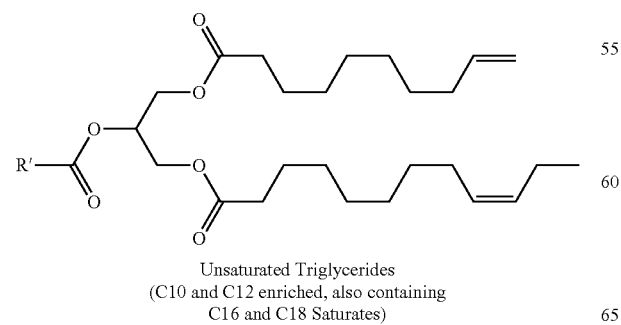

Unsaturated Triglycerides
(C10 and C12 enriched, also containing
C16 and C18 Saturates)

The procedure used to make UTG-0 is followed, except that palm oil is used instead of soybean oil.

MTG-0 Feedstock Derivatives

TABLE 5

Summary of Modified and Unsaturated Triglyceride Products

|  | Soybean Oil | | Palm Oil | |
| --- | --- | --- | --- | --- |
|  | Self-met. MTG-0 | X-met. UTG-0 | Self-met. PMTG-0 | X-met. PUTG-0 |
| TEA Ester, 1:1 | MTG-3 | UTG-3 | PMTG-3 | PUTG-3 |
| TEA Ester, 1:1 quat | MTG-7 | UTG-7 | PMTG-7 | PUTG-7 |
| TEA Ester, 2:1 | MTG-1 | UTG-1 | PMTG-1 | PUTG-1 |
| TEA Ester, 2:1 quat | MTG-2 | UTG-2 | PMTG-2 | PUTG-2 |
| TEA Ester, 3:1 | MTG-4 | UTG-4 | PMTG-4 | PUTG-4 |
| TEA Ester, 3:1 quat | MTG-8 | UTG-8 | PMTG-8 | PUTG-8 |
| MDEA Ester, 2:1 | MTG-9 | UTG-9 | PMTG-9 | PUTG-9 |
| MDEA Ester, 2:1 quat | MTG-10 | UTG-10 | PMTG-10 | PUTG-10 |

TEA = triethanolamine;
MDEA = N-methyldiethanolamine.

Esteramines from Modified and Unsaturated Triglycerides: General Procedure

Esteramines are prepared from modified triglycerides (MTG-0, PMTG-0) or unsaturated triglycerides (UTG-0, PUTG-0) using the following general procedure. Details of the preparation for the MTG products (MTG-1, -3, -4, and -9) appear in Table 6. The corresponding PMTG products are prepared analogously. Details of the preparation for the PUTG products (PUTG-1, -3, -4, and -9) also appear in Table 6, and the corresponding UTG products are prepared analogously.

In general, the triglyceride, alkanolamine (triethanolamine or N-methyldiethanolamine) and a base catalyst are combined in a 4-neck flask. The mixture is agitated (180 rpm) and heated rapidly to 175° C. under nitrogen. The mixture is allowed to react overnight and is then cooled to room temperature to give the esteramine. Residual unreacted alkanolamine is determined by titration of water-extractable amine with aqueous HCl. Amounts of reagents for selected esteramines appear in Table 6. The targeted product mixtures are also summarized below.

TABLE 6

Preparation of Esteramines from Modified or Unsaturated Triglycerides

| Esteramine | MTG-0, g | PUTG-0, g | TEA, g | MDEA, g | residual alkanolamine, % |
| --- | --- | --- | --- | --- | --- |
| MTG-1 | 230.6 | — | 70.4 | — | 3.88 |
| MTG-3 | 187.2 | — | 112.7 | — | 14.2 |
| MTG-4 | 249.8 | — | 51.1 | — | 1.38 |
| MTG-9 | 239.4 | — | — | 60.6 | 3.88 |
| PUTG-3 | — | 187.1 | 115.3 | — | 14.3 |
| PUTG-1 | — | 230.4 | 69.8 | — | 3.68 |
| PUTG-4 | — | 249.7 | 50.6 | — | 1.33 |
| PUTG-9 | — | 239.3 | — | 59.8 | 2.84 |

MTG-1: MTG TEA Ester (2:1)

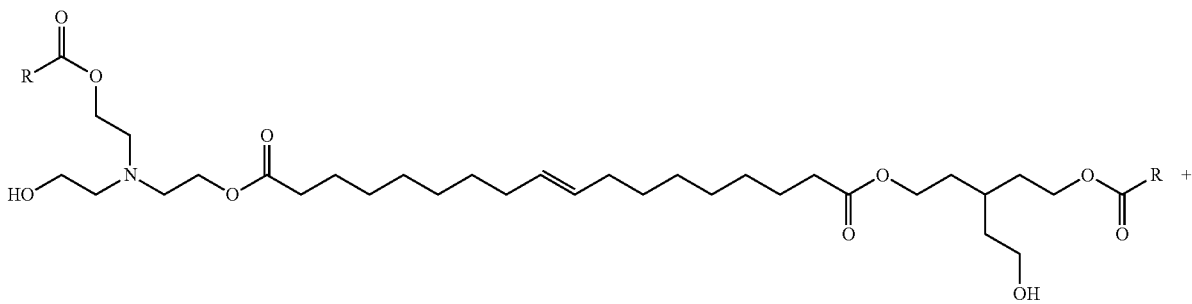

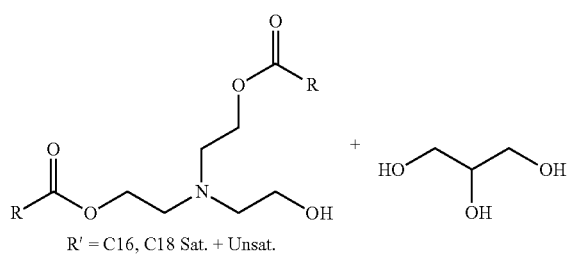

R' = C16, C18 Sat. + Unsat.

R = C16-C-18 Sat. and Unsat.

MTG-3: MTG TEA Ester (1:1)
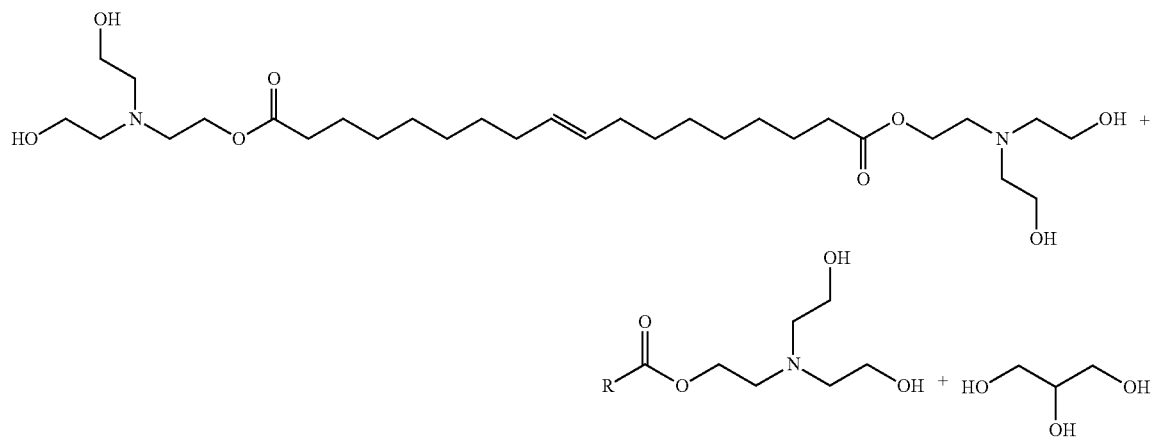
R = C16, C18 Sat. + Unsat.
MTG-4: MTG TEA Ester (3:1)
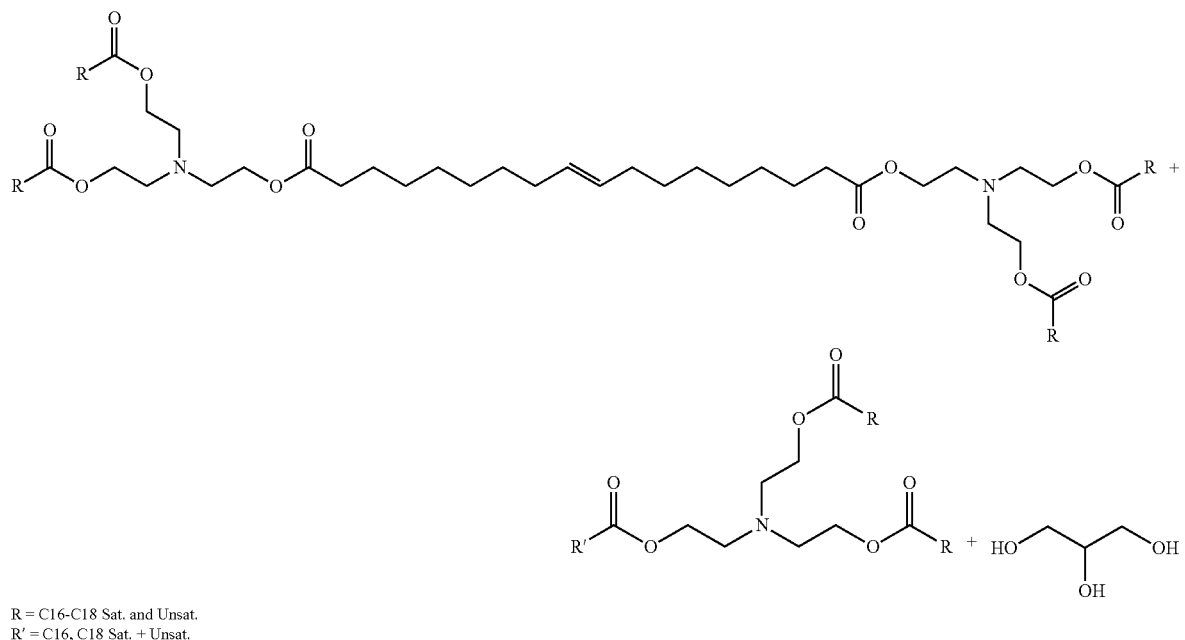
R = C16-C18 Sat. and Unsat.
R' = C16, C18 Sat. + Unsat.
MTG-9: MTG MDEA Ester (2:1)
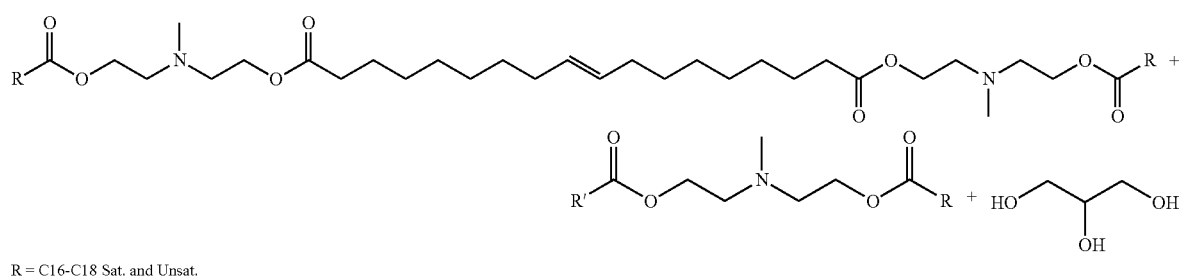
R = C16-C18 Sat. and Unsat.
R' = C16, C18 Sat. + Unsat.

PUTG-3: PUTG TEA Ester (1:1)

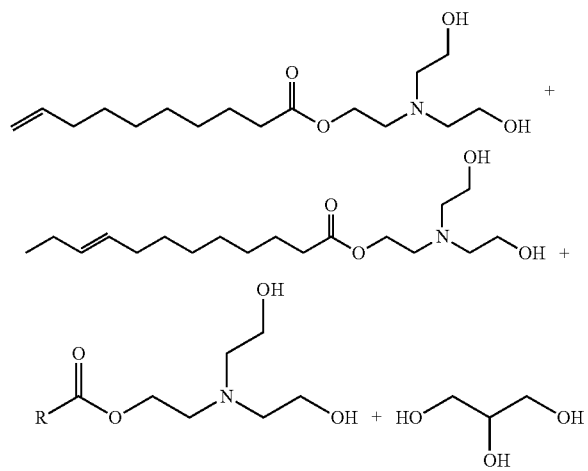

R = C16, C18 Sat. + Unsat.

PUTG-1: PUTG TEA Ester (2:1)

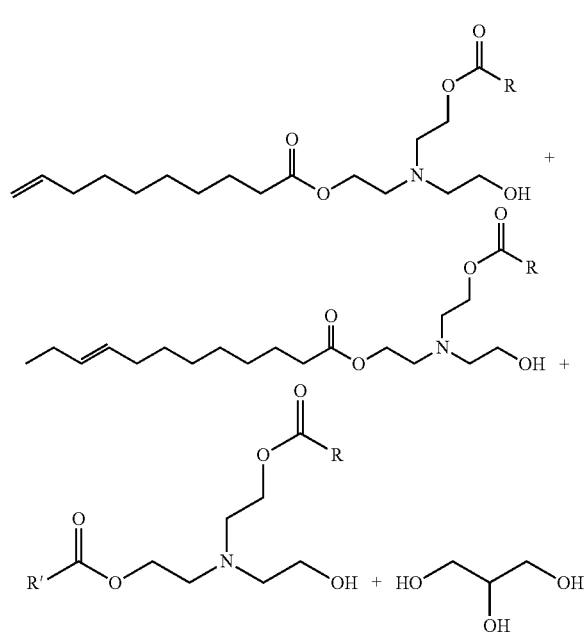

R = C10, C12-C18 Sat. and Unsat.
R' = C16, C18 Sat. + Unsat.

PUTG-4: PUTG TEA Ester (3:1)

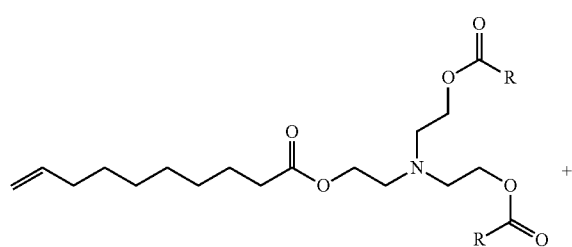

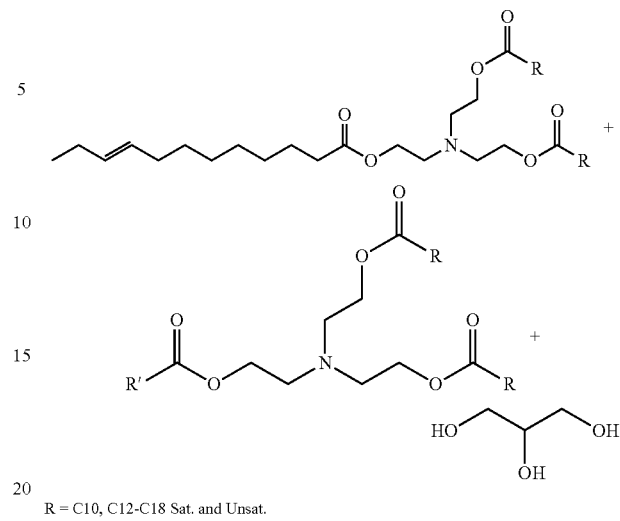

R = C10, C12-C18 Sat. and Unsat.
R' = C16, C18 Sat. + Unsat.

PUTG-9: PUTG MDEA Ester (2:1)

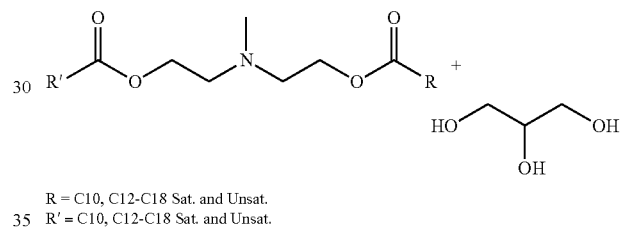

R = C10, C12-C18 Sat. and Unsat.
R' = C10, C12-C18 Sat. and Unsat.

Quaternization of Esteramines from Modified and Unsaturated Triglycerides:

General Procedure

The esteramines prepared from modified or unsaturated triglycerides are quaternized using the following general procedure. Details of the preparation for the MTG products (MTG-2, -7, -8, and -10) appear in Table 7. The corresponding PMTG products are prepared analogously. Details of the preparation for the PUTG products (PUTG-2, -7, -8, and -10) also appear in Table 7, and the corresponding UTG products are prepared analogously.

In general, the esteramine is charged to a round-bottom flask equipped with a condenser, thermocouple, heating mantle, and nitrogen inlet, and the contents are heated to 80° C. Dimethyl sulfate ("DMS") is added via addition funnel. Enough DMS is added to achieve >95% quaternization as determined from the perchloric acid titration (PAT) value. After the DMS addition, the temperature is raised to 85° C. One hour after the DMS addition is complete, the % quaternization is ~98%. Isopropyl alcohol (IPA) is added and the temperature is raised to 86° C. After 1 h, the mixture is cooled to room temperature and the ester quat is removed and tested with a Dräger apparatus for residual DMS. For the PUTG-8 preparation, the IPA is included in the initial charge, and the reaction temperature is adjusted downward to 65° C.-70° C. accordingly. Amounts of reagents for selected ester quats appear in Table 7. The targeted product mixtures are also summarized below.

TABLE 7
Quaternization of Esteramines from Modified or Unsaturated Triglycerides
| Ester Quat | Esteramine | Esteramine, g | DMS, g | IPA, g |
|---|---|---|---|---|
| MTG-2 | MTG-1 | 143.1 | 27.4 | 19.1 |
| MTG-7 | MTG-3 | 138.9 | 43.2 | 20.2 |
| MTG-8 | MTG-4 | 141.2 | 19.4 | 17.8 |
| MTG-10 | MTG-9 | 147.6 | 29.4 | 19.7 |
| UTG-2 | UTG-1 | 157.3 | 32.1 | 21.0 |
| PUTG-7 | PUTG-3 | 151.4 | 48.1 | 22.1 |
| PUTG-2 | PUTG-1 | 147.7 | 28.1 | 19.5 |
| PUTG-8 | PUTG-4 | 150.6 | 20.5 | 19.1 |
| PUTG-10 | PUTG-9 | 148.3 | 27.4 | 19.6 |
MTG-2 MTG TEA Ester (2:1) Quat
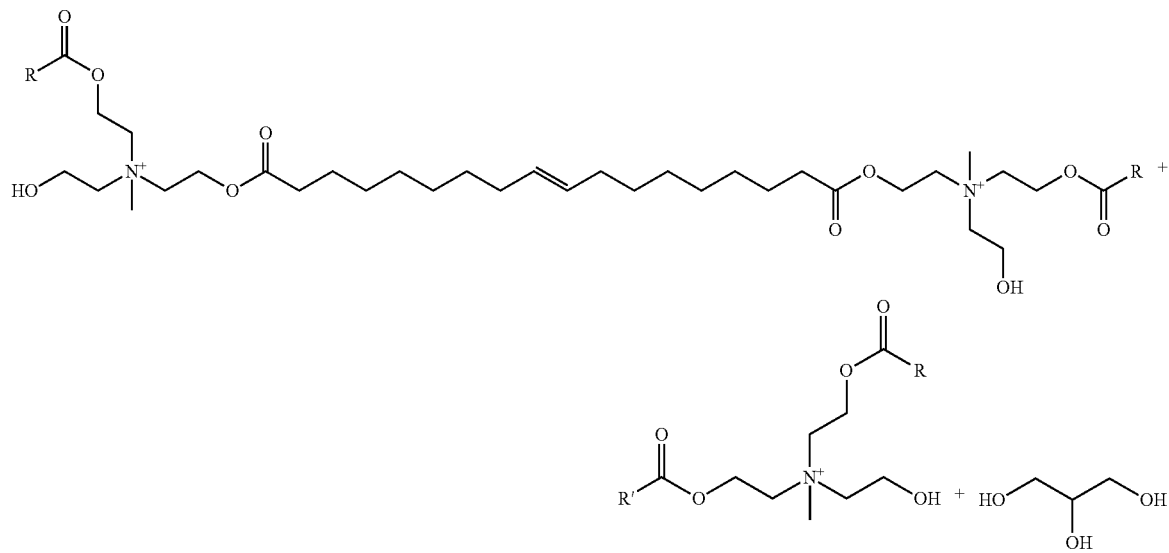
R = C16-C18 Sat. and Unsat.
R' = C16, C18 Sat. + Unsat.
MTG-7: MTG TEA Ester (1:1) Quat
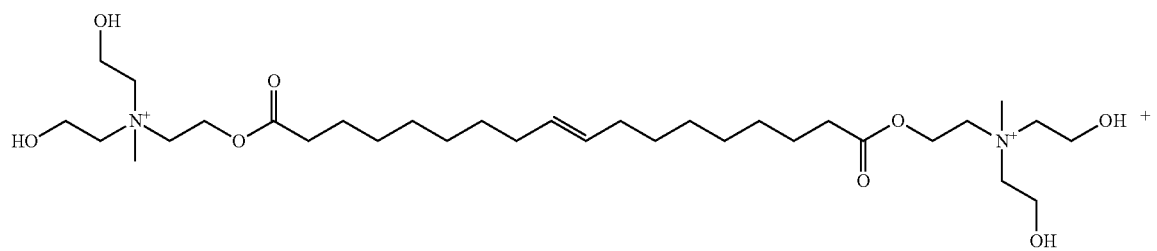
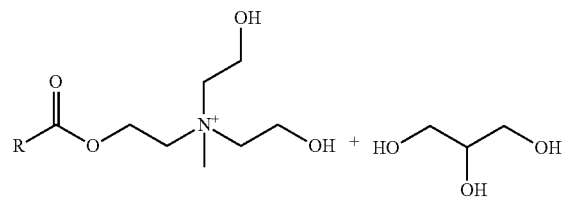
R = C16, C18 Sat. + Unsat.

MTG-8: MTG TEA Ester (3:1) Quat
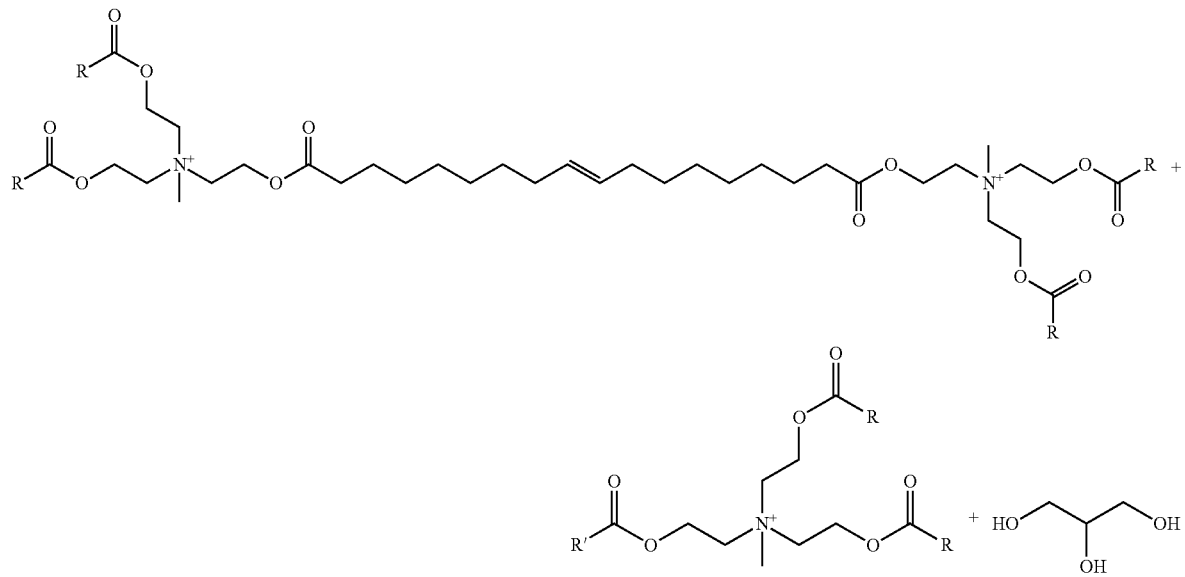
R = C16-C18 Sat. and Unsat.
R' = C16, C18 Sat. + Unsat.
MTG-10: MTG MDEA Ester (2:1) Quat
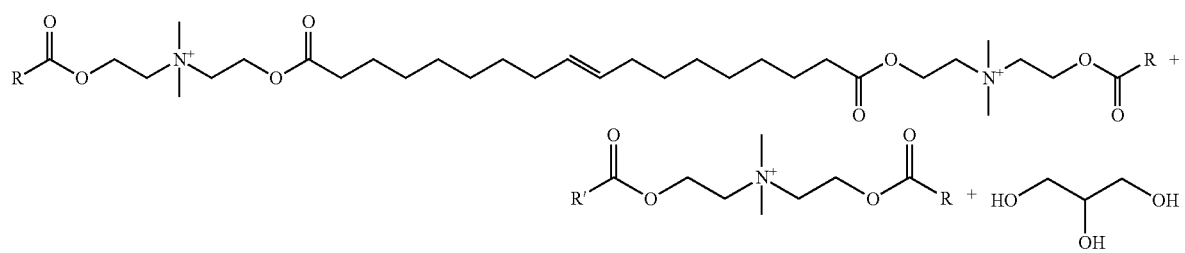
R = C16-C18 Sat. and Unsat.
R' = C16, C18 Sat. + Unsat.
PUTG-7: PUTG TEA Ester (1:1) Quat            PUTG-2 PUTG TEA Ester (2:1) Quat
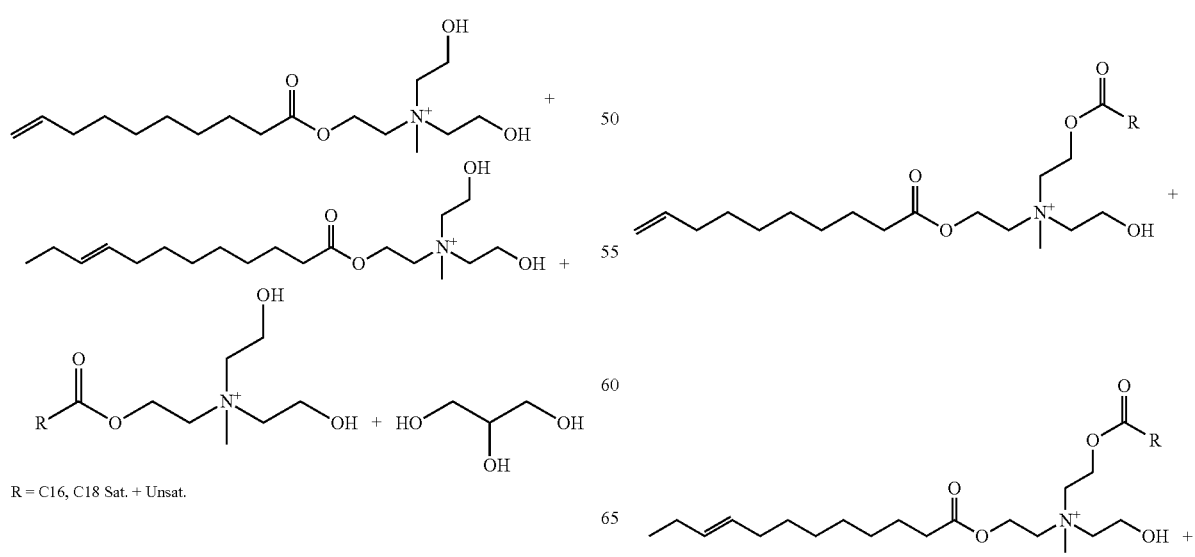
R = C16, C18 Sat. + Unsat.

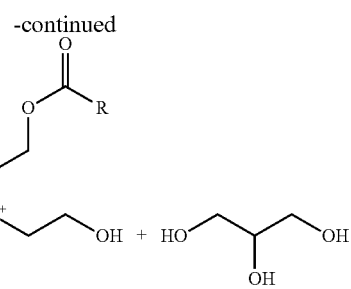

R = C10, C12-C18 Sat. and Unsat.
R' = C16, C18 Sat. + Unsat.

PUTG-8: PUTG TEA Ester (3:1) Quat

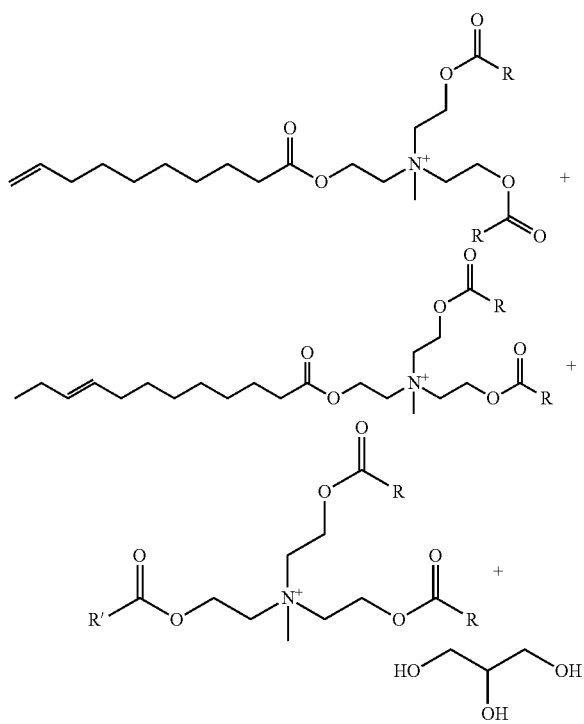

R = C10, C12-C18 Sat. and Unsat.
R' = C16, C18 Sat. + Unsat.

PUTG-10: PUTG MDEA Ester (2:1) Quat

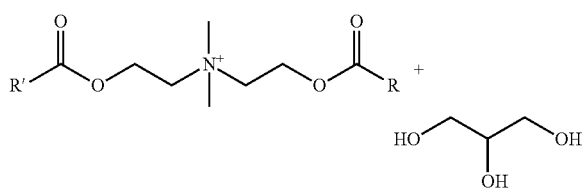

R = C10, C12-C18 Sat. and Unsat.
R' = C10, C12-C18 Sat. and Unsat.

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. A standard dilution test is conducted whereby the concentrates are diluted in water to determine if solubility is complete.

Control: Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 8 below.

Anionic test sample: Paraquat (4.57 g of 43.8% active material) is added to a 20-mL glass vial. An eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic test sample: Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (anionic/nonionic) test sample: Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Criteria for emulsion solubility: Test samples should be as good as or better than the control with no separation after one hour. Three test samples perform as well or better than the control in the emulsion stability test. Results appear in Table 8.

TABLE 8

Water Soluble Herbicide Formulation: Emulsion stability, mL separation

| test sample | Anionic | | | Nonionic | | | Adjuvant | | | Rating |
| --- | --- | --- | --- | --- | --- | --- | --- | --- | --- | --- |
| | sol | 1 h | 24 h | sol | 1 h | 24 h | sol | 1 h | 24 h | |
| C10-7 | S | 0 | 0 | S | 0 | 0 | S | 0 | 0 | good |
| C12-7 | S | 0 | 0 | D | 0 | 0 | S | 0 | 0 | good |
| Mix-16 | S | 0 | 0 | D | Tr | Tr | S | 0.25 | 0.25 | good |

D = dispersable;
S = soluble;
I = insoluble;
Tr = trace
Control result: Solubility: D; 1 h: 0 mL; 24 h: Tr.

Agricultural Dispersant Screening:

The potential of a composition for use as an agricultural dispersant is evaluated by its performance with five typical pesticide active ingredients: Atrazine, Chlorothalonil, Diuron, Imidacloprid and Tebuconazole. The performance of each dispersant sample is evaluated in comparison with five standard Stepsperse® dispersants: DF-100, DF-200, DF-400, DF-500, and DF-600 (all products of Stepan Company), and each is tested with and without a nonionic or anionic wetting agent. Overall results versus the controls are summarized in Table 9; four esteramines perform at least as well as the controls. Details of the individual tests are reported in Table 10 (wetting agent included) and Table 11 (no wetting agent). Note that sample C12-3 receives an overall rating of "good" when the results with and without the wetting agent are taken into account.

A screening sample is prepared as shown below for each active. Wetting agents, clays, and various additives are included or excluded from the screening process as needed. The weight percent of pesticide ("technical material") in the formulation depends on the desired active level of the final product. The active level chosen is similar to other products on the market. If this is a new active ingredient, then the highest active level is used.

Samples are evaluated in waters of varying hardness, in this case 342 ppm and 1000 ppm. The initial evaluations are performed at ambient temperature. Other temperatures can be evaluated as desired. The 342 ppm water is made by dissolving anhydrous calcium chloride (0.304 g) and magnesium chloride hexahydrate (0.139 g) in deionized water and diluting to 1 L. The 1000 ppm water is made similarly using 0.89 g of calcium chloride and 0.40 g of magnesium chloride hexahydrate.

Technical material (60-92.5 wt. %), wetting agent (0.5-1.0 wt. % when used), silica (0.5-1.0 wt. %), and clay (balance) are blended in a suitable container. The blend is milled to a particle size of at least a d (90) of <20μ using a hammer and air/jet mills as needed. Test dispersant (0.1 g) is added to test water (50 mL) in a beaker and stirred 1-2 min. Milled powder containing the technical material (1.0 g) is added to the dispersant solution and stirred until all powder is wet (2-5 min.). The mixture is transferred to a 100-mL cylinder using additional test water for rinsing the beaker and is then diluted to volume. The cylinder is stoppered and inverted ten times, then allowed to stand. Visual inspection is performed at t=0.5, 1.0, 2.0, and 24 hours, and the amount of sediment observed (in mL) is recorded. Trace of sediment="Tr" (see Tables 10-11).

TABLE 9

Overall Performance as an Agricultural Dispersant

| Sample | Rating |
|---|---|
| C10-5 | Superior |
| C12-3 | Good |
| C12-5 | Good |
| C12-7 | Good |
| Controls | Good |

TABLE 10

Agricultural Dispersants Testing: Nonionic or Anionic Wetting Agent Included
Sedimentation results at 1 h; 24 h (mL)

|  | test water, ppm | DF-200 (anionic) | DF-500 (anionic) | C12-3 (nonionic) | C12-5 (nonionic) | C12-7 (anionic) |
|---|---|---|---|---|---|---|
| Diuron | 342 | 0.25-0.5; 1 | Tr; 1 | 0.75; 1.25 | 0.5-1; 1 | 1.5; 2 |
|  | 1000 | 0.5-1; 1-1.25 | 2-2.5; 2 | 0.25-0.5; 0.75 | 0.5-1; 1 | 2.25; 2 |
| Chlorothalonil | 342 | 0.25; 1.5 | Tr; 1.25 | 0.5; 2 | 0.5; 1 | Tr; 1 |
|  | 1000 | Tr; 1.75 | 5; 3.5 | Tr-0.5; 1-1.25 | 0.5; 1 | Tr; 0.75 |
| Imidacloprid | 342 | Tr; 1-1.5 | Tr; 1.5-2 | Tr-0.25; 1 | 0.75-1; 1-1.5 | 1; 1.75-2 |
|  | 1000 | Tr; 2 | 1-1.5; 3 | Tr-0.25; 1 | 0.75-1; 2 | 0.5-1; 1.5-2 |
| Tebuconazole | 342 | 0; 1 | Tr; 1 | Tr; 0.5 | Tr; 1 | 3; 3.5 |
|  | 1000 | 0.5-1; 3.5-4 | 12; 5 | 5.25; 3 | Tr; 1 | 3.5; 3.5-3.75 |
| Atrazine | 342 | Tr; 1 | Tr; 1 | Tr-0.25; 1.5 | 0.25-0.5; 1-1.5 | 0.25-0.5; 1.75-2 |
|  | 1000 | Tr; 2 | 7; 4 | 0.25; 1 | 0.5-1; 2 | 0.25-0.5; 1 |
| Rating |  | control | control | good | good | good |

TABLE 11

Agricultural Dispersants Testing: No Wetting Agent
Sedimentation results at 1 h; 24 h (mL)

|  | test water, ppm | DF-200 | DF-500 | C10-5 | C12-3 |
|---|---|---|---|---|---|
| Diuron | 342 | 1; 2 | 0.5; 1-1.5 | 0.25-0.5; 1 | 0.75-1; 1.5 |
|  | 1000 | 1; 2-2.5 | 0.5-0.75; 2 | 0.25-0.5; 0.75-1 | 2.5-3; 2-2.5 |
| Chlorothalonil | 342 | 0.25; 1-1.25 | 0.25; 1-1.25 | 0.25-0.5; 1.25-1.5 | 5-5.5; 4 |
|  | 1000 | 0.25-0.5; 1.25-1.5 | 2; 3 | 0.25-0.5; 1-1.25 | 5-5.25; 4 |
| Imidacloprid | 342 | Tr; 1-1.5 | 0.5-1; 2 | 0.75-1; 1-1.25 | 0.5-0.75; 1.5-2 |
|  | 1000 | Tr; 1-1.5 | 0.5-1; 2-2.5 | 0.5-0.75; 1-1.25 | 2-2.25; 2 |
| Tebuconazole | 342 | Tr; 1.25 | Tr; 1.5 | 0; 0.25-0.5 | 0.5-0.75; 2-2.5 |
|  | 1000 | Tr; 3 | Tr; 3 | 0; 0.5-0.75 | 5; 4.5-5 |
| Atrazine | 342 | Tr-0.25; 1-1.5 | 0.5; 1 | Tr-0.25; 0.75-1 | 1.5-2; 3 |
|  | 1000 | Tr-0.25; 1-1.5 | 6; 3 | Tr-0.25; 0.75-1 | 3; 4 |
| Rating |  | control | control | superior | inferior |

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

A neutral, dilutable all-purpose cleaner is prepared from propylene glycol n-propyl ether (4.0 g), butyl carbitol (4.0 g), sodium citrate (4.0 g), Stepanol® WA-Extra PCK (sodium lauryl sulfate, Stepan, 1.0 g), test sample (0.90 g if 100% active material), and deionized water (to 100.0 g solution). The control sample for nonionic/amphoteric testing replaces the test sample with Bio-Soft® EC-690 (ethoxylated alcohol, Stepan, 1.0 g, nominally 90% active material).

Soil Composition:

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica 1 (8), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening (product of J. M. Smucker Company) (1), olive oil (3), linoleic acid (3), and squalene (3).

Four samples, Mix-3, Mix-5, Mix-15, and UTG-7, perform equal to their corresponding controls in this test (see Tables 12A and 12B).

TABLE 12A

Control Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 4 | 52.5 | 58.2 | 59.5 | 60.9 | 63.3 |
| Control 18 | 62.2 | 67.6 | 70.4 | 71.7 | 71.7 |
| Control 19 | 60.8 | 68.0 | 70.6 | 71.4 | 71.5 |

TABLE 12B

Nonionic/Amphoteric Test Samples: Inventive Examples

| Sample | Con. # | Compound class | Ave. % clean | | | | | Rating |
|---|---|---|---|---|---|---|---|---|
| | | | 2 | 4 | 6 | 8 | 10 | |
| Mix-3 | 19 | TEA ester | 55.0 | 61.6 | 63.3 | 65.6 | 66.7 | equal |
| Mix-5 | 4 | TEA ester | 60.1 | 62.0 | 64.7 | 66.3 | 67.1 | equal |
| Mix-15 | 18 | DMEA ester | 47.0 | 60.9 | 62.8 | 64.3 | 65.5 | equal |
| UTG-7 | 4 | TEA ester quat | 59.5 | 62.7 | 63.7 | 66.0 | 66.4 | equal |

Hair Conditioners: Procedure for Evaluation of Wet Combability

Hair tresses (10" lengths, 2-3 g) are prepared using a consistent and uniform hair type (double-bleached, blond). The tresses are collectively shampooed with a 15% active sodium lauryl sulfate solution. Care is taken to avoid excessive tangling during shampooing. The tresses are rinsed clean with 40° C. tap water. The process is repeated to simulate a double shampoo application. The tresses are separated and tagged for testing. The conditioner preparation (2.0 cm$^3$), whether it be the test or the control, is applied to each clean, wet tress using a syringe. When the test material is an unquaternized esteramine, the base conditioner used as a control for the testing contains cetyl alcohol (2.0%), hydroxyethyl cellulose (0.7%), cetrimonium chloride (1.0%), potassium chloride (0.5%), and water (qs to 100%). The unquaternized esteramine is formulated as a 2 wt. % (actives) additive to the base conditioner. When the test material is a quaternized esteramine, the conditioner used as a control for testing contains cetyl alcohol (3%), cetrimonium chloride (1%), and water (qs to 100%). The quaternized esteramine is formulated at 1% active into a conditioner that contains cetyl alcohol (3%) and water (qs to 100%).

The conditioner is worked through the hair for one minute with downward finger strokes. The tresses are rinsed thoroughly clean under 40° C. tap water. Excess water is squeezed from each tress to simulate towel-dry hair. The hair is combed through, at first, in the wet state. Ease of combing is evaluated for the test samples and the base or control conditioner, and qualitative ratings are assigned to the test samples in comparison to the results with base or control conditioner only.

When the material is an unquaternized esteramine, enhancement of conditioning of the base by the esteramine additive is the technical success criteria at this stage and is the basis for a superior rating. Equal to lower performance versus the base conditioner earns an inferior rating.

When the material is a quaternized esteramine, the rating system is as follows: "superior" is an improvement of wet combing above that of the conditioner used as a control for testing; "equal" is wet combing comparable to the conditioner used as a control for testing; and "inferior" is wet combing worse than the conditioner used as a control for testing. Results appear in Table 13.

TABLE 13

Wet Combability Performance in Hair Conditioners

| Superior | | Good |
|---|---|---|
| MTG-1 | PUTG-1 | Base conditioner |
| UTG-4 | PUTG-4 | PMTG-7* |
| PMTG-1 | PUTG-7* | |
| PMTG-4 | PUTG-9 | |
| PMTG-9 | | |

*quaternized esteramines

Personal Care: Cleansing Application

Viscosity and mechanical shake foam tests are used to assess the likely value of a particular surfactant as a secondary surfactant in cleansing applications for personal care.

All experimental samples are evaluated for their performance versus a control (either cocamide MEA or cocamidopropylbetaine).

Viscosity curves are generated by preparing aqueous solutions of the test material or the control with 12% active sodium lauryl ether (1) sulfate (SLES-1), then measuring viscosity by means of a Brookfield DV-1+ viscometer. The active contents of test material are 1.5% if the material is an amidoamine, and 3% if the material is an amidoamine oxide. Sodium chloride is added incrementally (1-3 wt. %) and viscosity is recorded as a function of increasing NaCl concentration. A "good" result is a curve that shows a viscosity build comparable to the control sample. A "superior" rating indicates that the sample builds viscosity substantially more rapidly than the control.

Foaming properties are evaluated using a mechanical shake foam test. Aqueous solutions composed of 12% active SLES-1 and the test material or control (1.5% active content if material is an amidoamine, 3% active content if material is an amidoamine oxide) are prepared. Sample solutions calculated at 0.2% total surfactant active are thereafter made from the aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to settle for 15 s. Foam height is recorded. After 5 min., foam height is recorded again. The experiment is repeated without the castor oil. In one set of experiments, the cleansing base contains SLES-1 in both the experimental and control runs. In a second set of experiments, the cleansing base contains another widely used anionic surfactant, i.e., a mixture of sodium methyl 2-sulfolaurate and disodium 2-sulfolaurate, instead of SLES-1. A "good" result is recorded when the solution containing the test material results in foam heights that are within +/−25 mL of the control runs. Results >25 mL of the control garner a superior rating; results <25 mL of the control are rated inferior.

MTG-1, when tested against cocamidopropyl betaine, demonstrates equal foaming and viscosity building properties, and is rated "good" overall.

Personal Care/Antibacterial Handsoap:
Method to Determine Foam Enhancement Benefit Foam volume, which signals "clean" to consumers, is a desirable attribute in an antibacterial handsoap. Because cationic antibacterial actives are not compatible with anionic surfactants (the best foamers), achieving sufficient foam volume with them is challenging. The method below identifies surfactants that provide more foam volume than cocamidopropylbetaine (actives/actives basis) in an antibacterial handsoap base. Formulation: deionized water (q.s. to 100 wt. %), cocoglucoside (3.0 wt. %), lauramine oxide (3.0 wt. %), benzalkonium chloride (0.1 wt. %), and test molecule or cocamidopropylbetaine (3.0 wt. %).

Solutions are prepared by combining ingredients in the order prescribed above, stirring with a stir bar or mixing gently using an overhead stirrer or manually using a spatula. Heat may be applied if the test molecule is a solid at room temperature. Mixing is maintained to ensure a homogenous solution. The pH is adjusted to 6.5+/−0.5.

Test and control solutions are compared, with and without 2% castor oil, at 0.2% total surfactant active concentration (2.22 g solution to 100 mL with tap water from Lake Michigan, ~150 ppm Ca/Mg hardness) for foam volume using the cylinder inversion test. Initial and delayed (5 min.) measurements are taken.

Rating system: Superior: a result >25 mL over the cocamidopropylbetaine control in both oil and no-oil systems. Good: a result within 25 mL of the cocamidopropylbetaine control in both oil and no-oil systems. Inferior: a result >25 mL below that of the cocamidopropylbetaine control in both oil and no-oil systems.

Compared with the controls, three samples, C10-5, C12-7, and UTG-2 all show good overall performance in the antibacterial handsoap tests.

Oilfield Corrosion Inhibition: Polarization Resistance Procedure

Polarization resistance is run in dilute NACE brine (3.5 wt. % NaCl; 0.111 wt. % $CaCl_2.2H_2O$; 0.068 wt. % $MgCl_2.6H_2O$) under sweet conditions ($CO_2$ sparged) at 50° C. The working electrode is cylindrical, made of C1018 steel, and rotates at 3000 rpm. The counter electrode is a platinum wire. The reference is a calomel electrode with an internal salt bridge. A baseline corrosion rate is established over at least a 3-h period. Once the baseline has been established, the corrosion inhibitor is injected and data is collected for the remainder of the test period. The desired inhibitor concentration is 0.00011-0.0010 meq/g active. Software details: initial delay is on at 1800 s with 0.05 mV/s stability; range: −0.02 to +0.02V; scan rate: 0.1 mV/s; sample period: 1 s; data collection: ~24 h. The final corrosion rate is an average of the last 5-6 h of data collection. Protection rate is calculated from:

$$\text{Protection Rate} = \frac{(\text{Initial Protection Rate[no inhibitor]} - \text{Final Protection Rate [with inhibitor]}) * 100}{\text{Initial Protection Rate [no inhibitor]}}$$

As shown in Table 14, twenty-one of the tested samples show overall performance as corrosion inhibitors that equals or exceeds that of the control.

TABLE 14

Performance in EOR Corrosion Inhibitors

| Sample | Protection Rate (%) | | | Overall Rating |
|---|---|---|---|---|
| | Low Dose | Mid Dose | High Dose | |
| Industry Std. A | 85 | 85 | 80 | |
| Control B | 66 | 83 | 76 | |
| Control C | 97 | 98 | 97 | |
| Control D | 90 | 98 | 85 | |
| C10-5 | 90 | 72 | 61 | good |
| C12-5 | 80 | 89 | 90 | good |
| C16-7 | 80 | 73 | 78 | good |
| Mix-4 | 84 | 88 | 89 | good |
| Mix-6 | 91 | 90 | 80 | good |
| Mix-10 | 79 | 85 | 82 | good |
| MTG-2 | 59 | 95 | 89 | good |
| MTG-7 | 80 | 89 | 81 | good |
| MTG-8 | 16 | 77 | 95 | good |
| MTG-10 | 72 | 72 | 50 | good |
| PMTG-2 | 71 | 85 | 90 | good |
| PMTG-7 | 98 | 84 | 73 | good |
| PMTG-8 | 96 | 98 | 99 | good |
| PMTG-10 | 93 | 85 | 89 | good |
| UTG-2 | 95 | 91 | 89 | good |
| UTG-7 | 92 | 86 | 90 | good |
| UTG-10 | 87 | 95 | 93 | superior |
| PUTG-2 | 93 | 91 | 90 | good |
| PUTG-7 | 94 | 87 | 63 | good |
| PUTG-8 | 71 | 90 | 83 | good |
| PUTG-10 | 94 | 76 | 70 | good |

The preceding examples are meant only as illustrations. The following claims define the invention.

We claim:
1. A composition comprising an esteramine having a structure selected from the group consisting of:
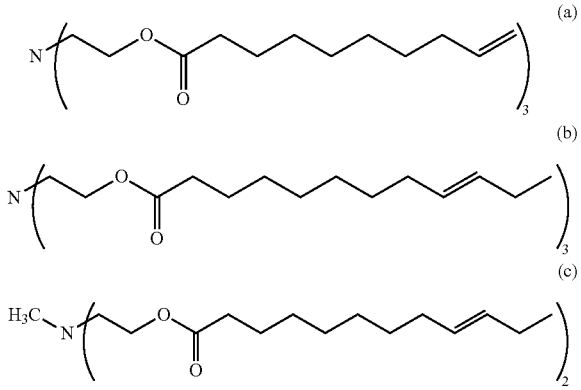
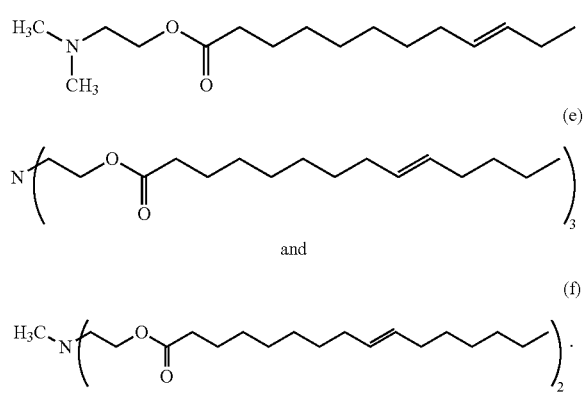
and
2. A composition comprising an esteramine quat having a structure selected from the group consisting of:
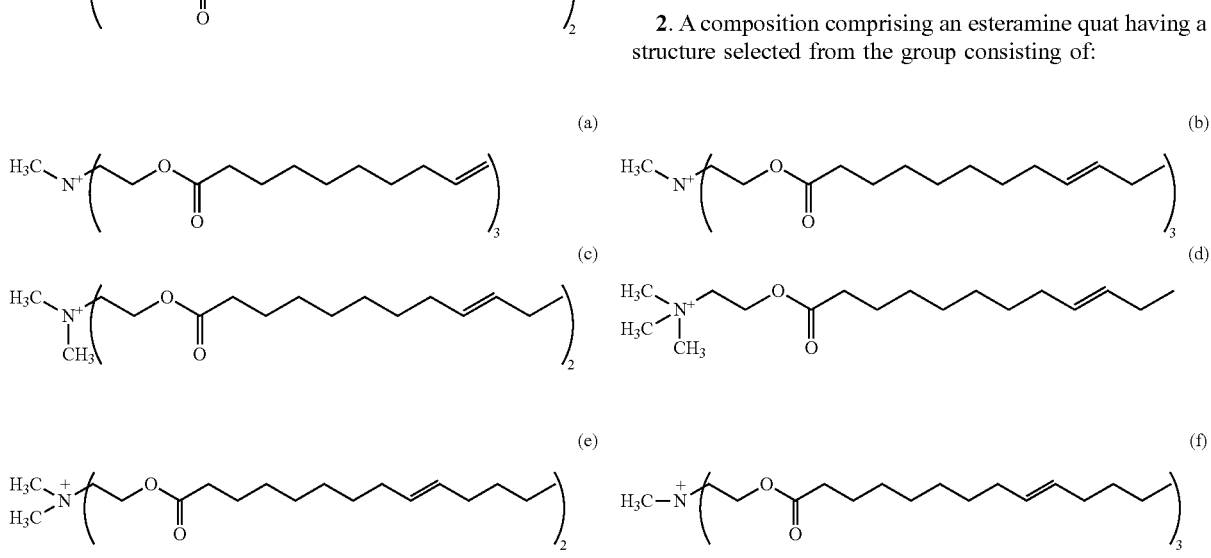
and
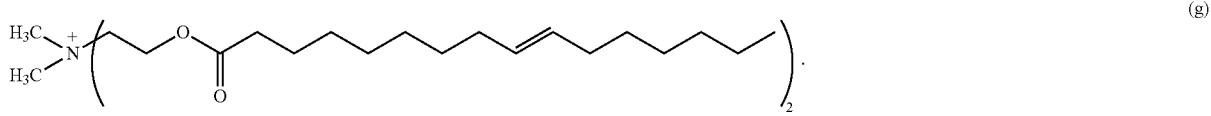
3. A composition comprising an esteramine or an esteramine quat having a structure selected from the group consisting of:
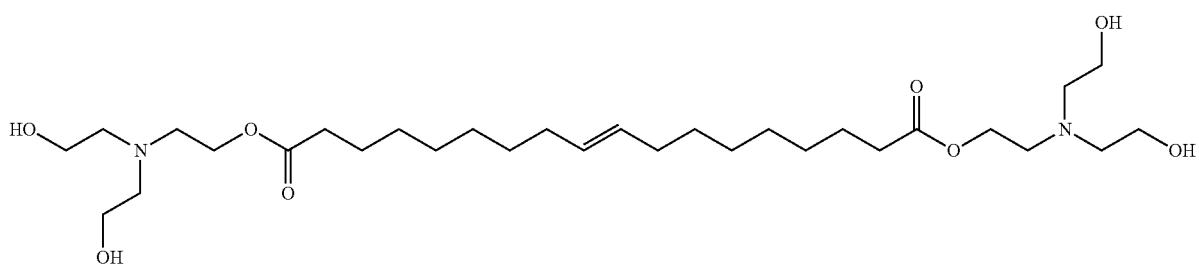

(b)
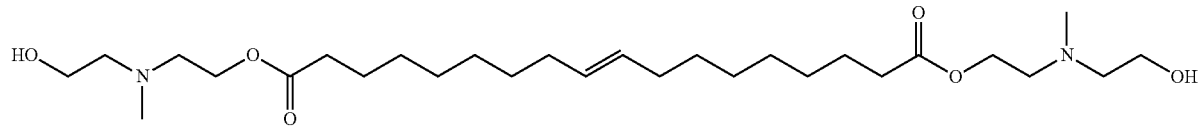
(c)
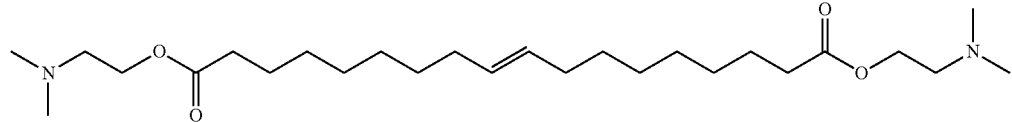
(d)
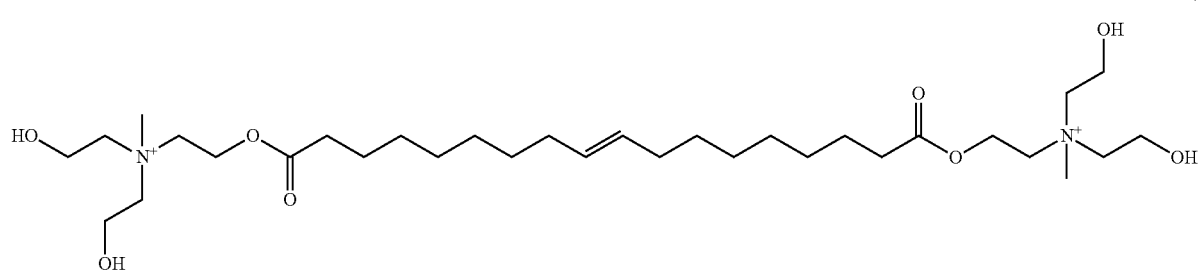 [SMILES: C[N+](CCO)(CCO)CCOC(=O)CCCCCCC/C=C/CCCCCCCC(=O)OCC[N+](C)(CCO)CCO]
(e)
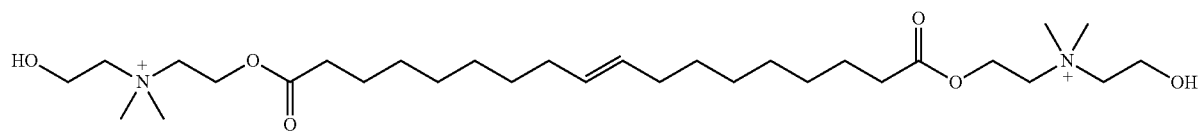
and
(f)
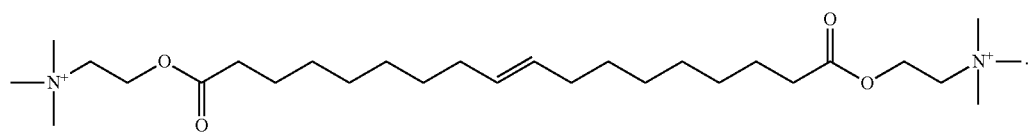
40
4. A composition comprising an esteramine or an esteramine quat from a modified triglyceride and having a structure selected from the group consisting of:
(a)
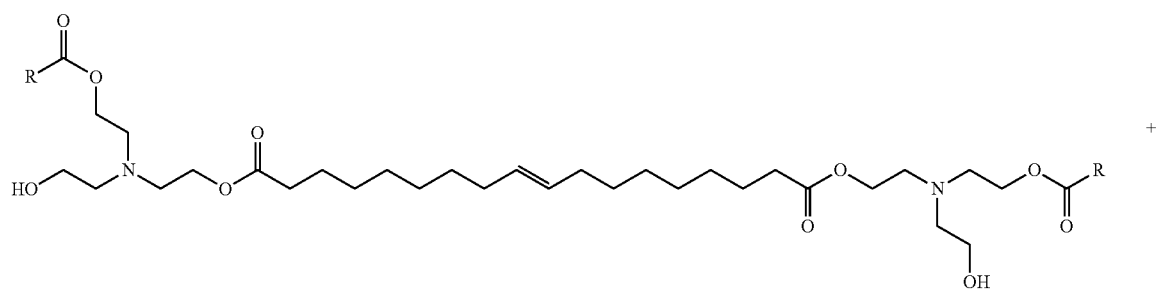
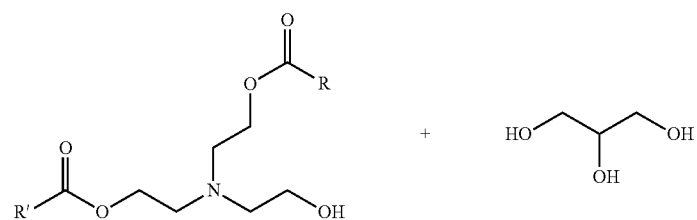

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group;
(b)
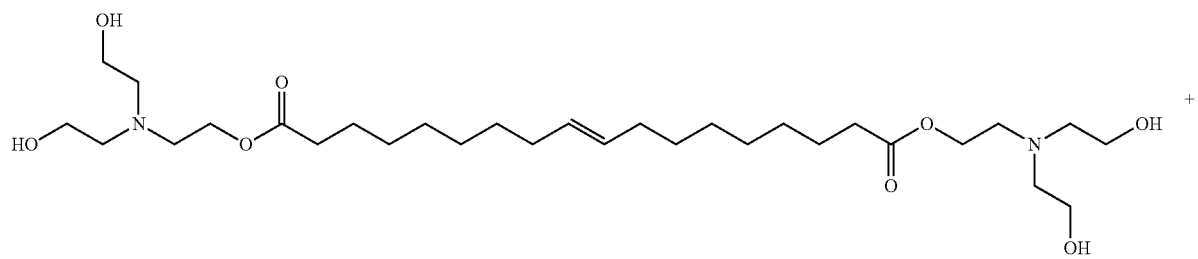
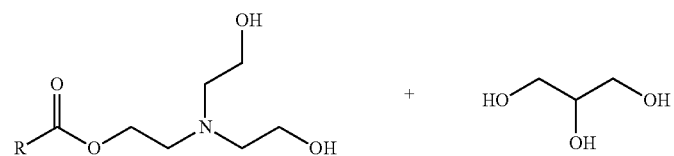
wherein R is a saturated $C_{16}$ or $C_{18}$ group or an unsaturated $C_{16}$ or $C_{18}$ group;
(c)
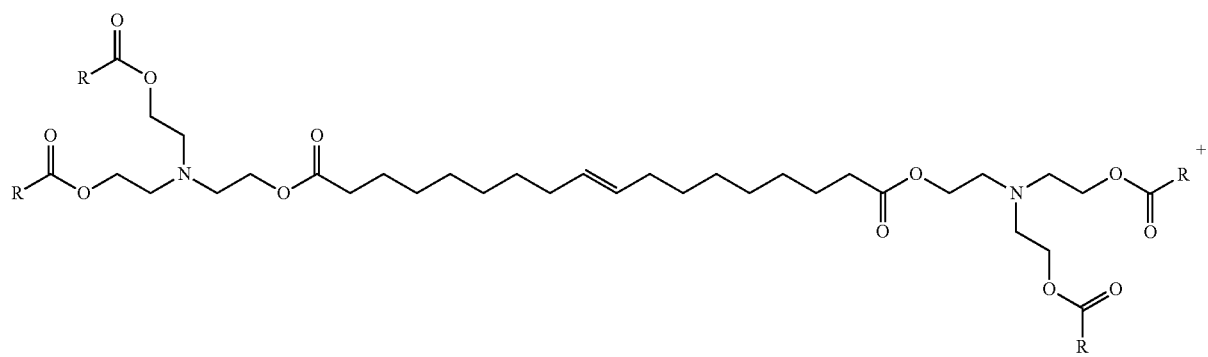
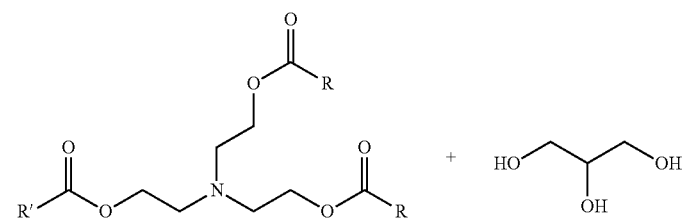

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group;

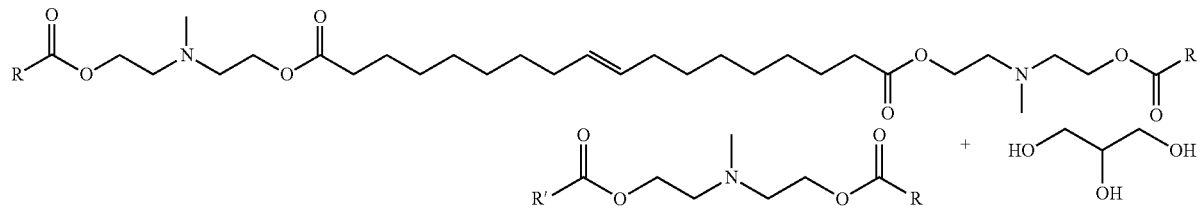
(d)

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group;

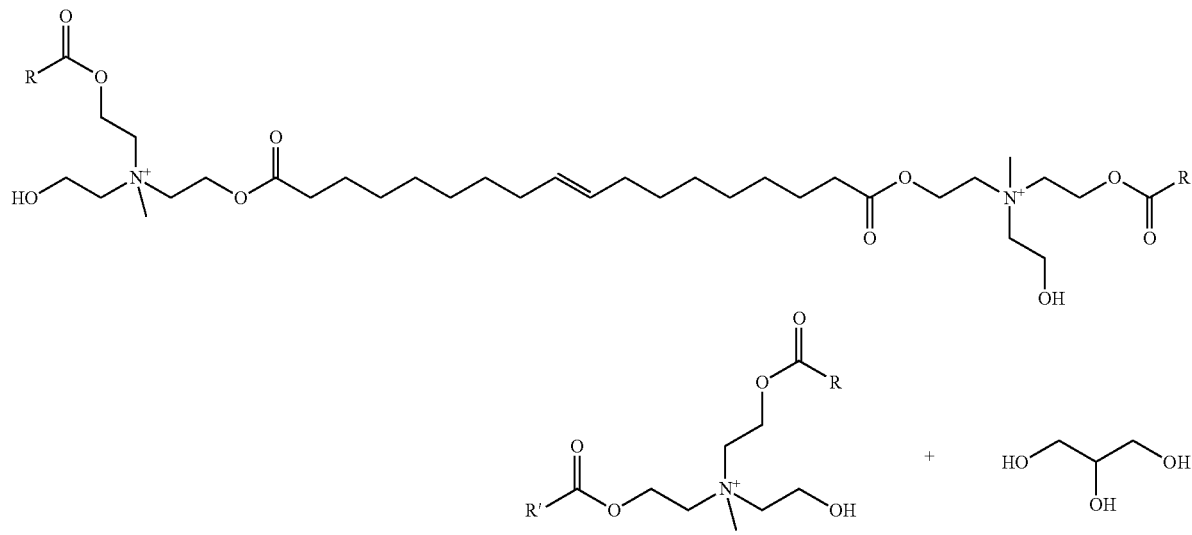
(e)

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group;

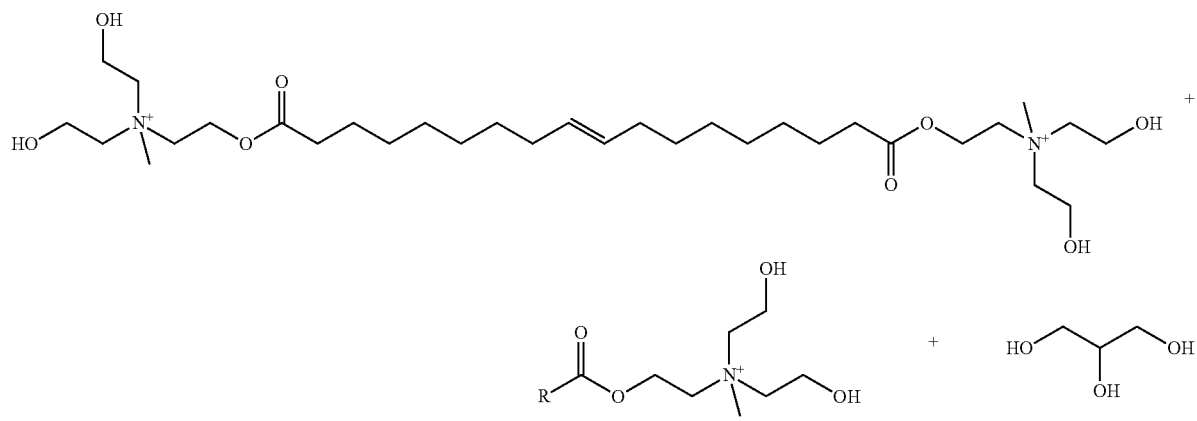
(f)

wherein R is a saturated $C_{16}$ or $C_{18}$ group or an unsaturated $C_{16}$ or $C_{18}$ group;

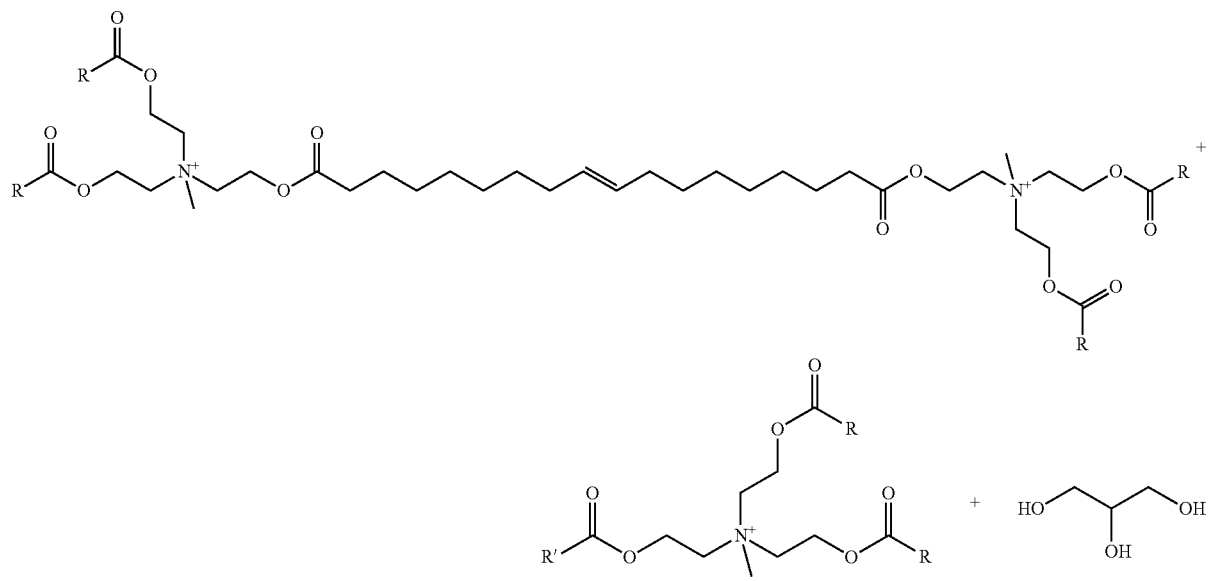

(g)

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group;
and

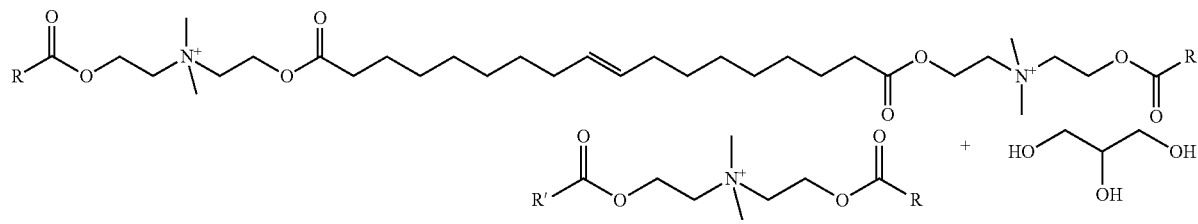

(h)

wherein R' is a saturated $C_{16}$ or $C_{18}$ group or an unsaturated $C_{16}$ or $C_{18}$ group; and
wherein R is a saturated $C_{16}$ or $C_{18}$ group or an unsaturated $C_{16}$ or $C_{18}$ group.

5. A composition comprising an esteramine or an esteramine quat from a unsaturated triglyceride and having a structure selected from the group consisting of:

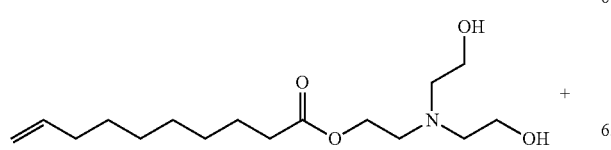

(a)

-continued

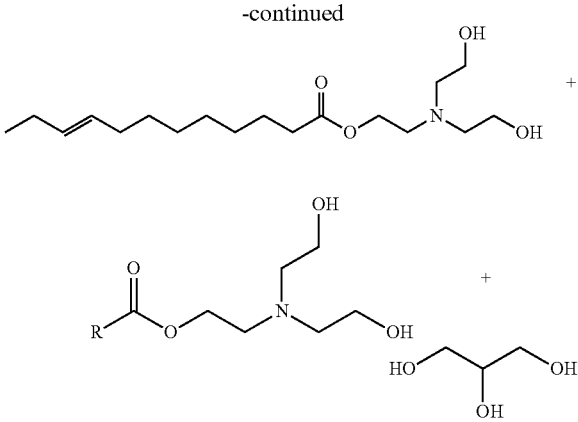

wherein R is a saturated $C_{16}$ or $C_{18}$ group or an unsaturated $C_{16}$ or $C_{18}$ group;

(b)

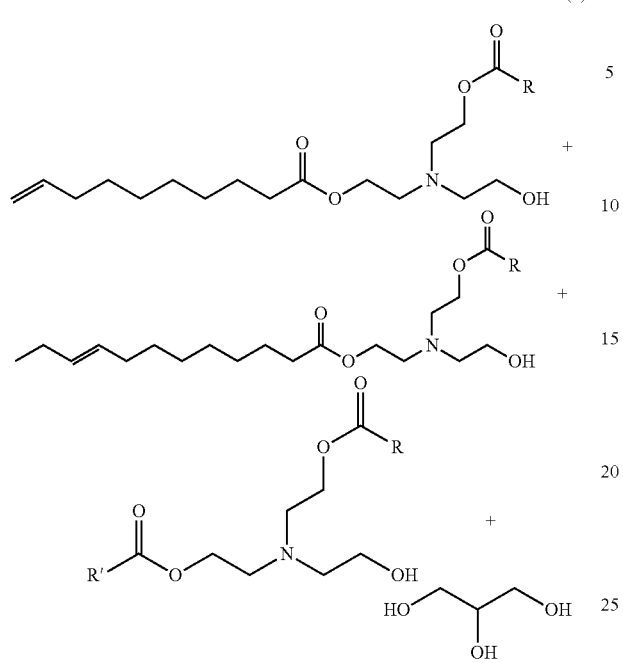

wherein R' is a saturated $C_{16}$ or $C_{18}$ group or an unsaturated $C_{16}$ or $C_{18}$ group; and wherein R is a saturated $C_{10}$ group or a saturated $C_{12}$ to $C_{18}$ group or an unsaturated $C_{10}$ group or an unsaturated $C_{12}$ to $C_{18}$ group;

(c)

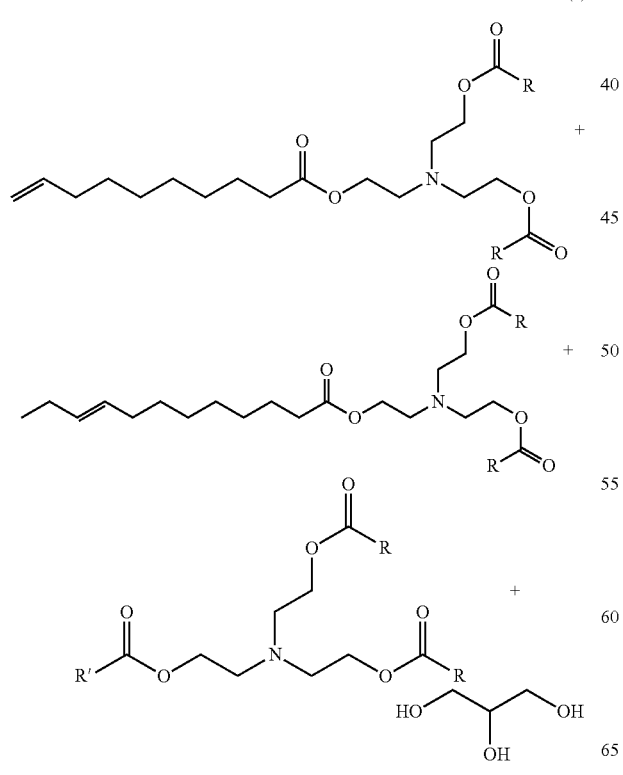

(d)

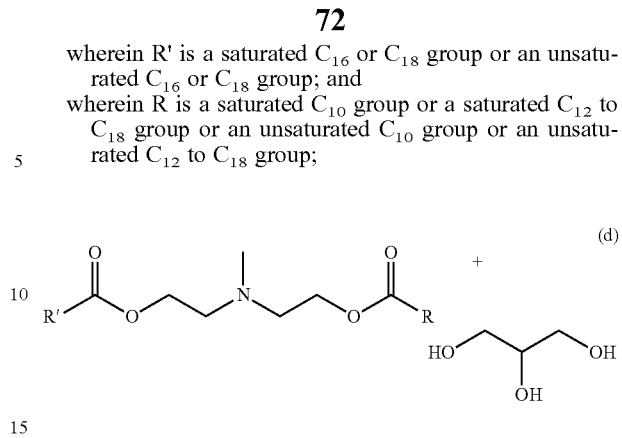

wherein R is a saturated $C_{10}$ group or a saturated $C_{12}$ to $C_{18}$ group or an unsaturated $C_{10}$ group or an unsaturated $C_{12}$ to $C_{18}$ group;
and wherein R' is a saturated $C_{10}$ group or a saturated $C_{12}$ to $C_{18}$ group or an unsaturated $C_{10}$ group or an unsaturated $C_{12}$ to $C_{18}$ group;

(e)

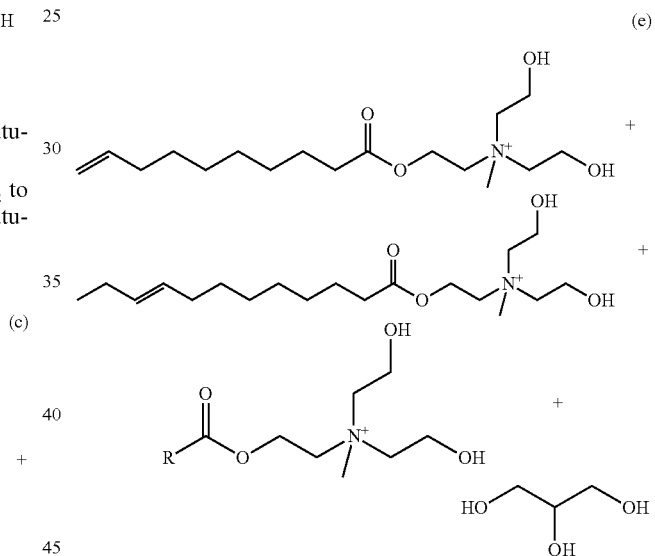

wherein R is a saturated $C_{16}$ or $C_{18}$ group or an unsaturated $C_{16}$ or $C_{18}$ group;

(f)

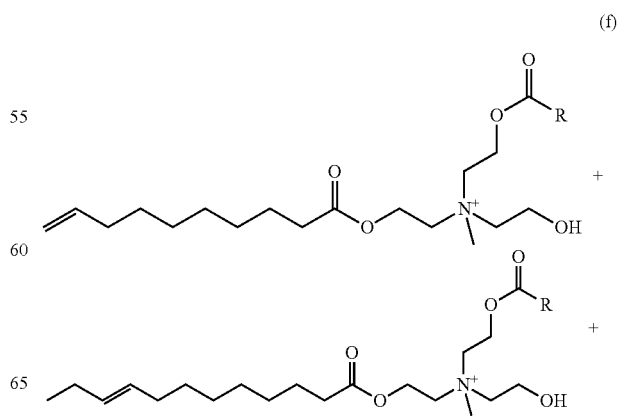

-continued

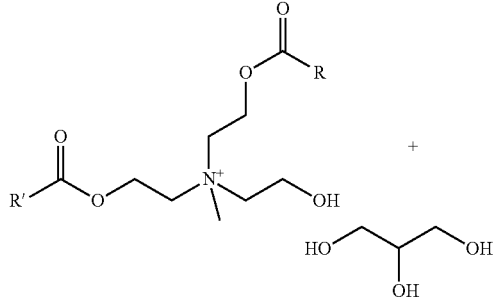

wherein R' is a saturated $C_{16}$ or $C_{18}$ group or an unsaturated $C_{16}$ or $C_{18}$ group; and wherein R is a saturated $C_{10}$ group or a saturated C12 to C18 group or an unsaturated $C_{10}$ group or an unsaturated $C_{12}$ to $C_{18}$ group;

(g)

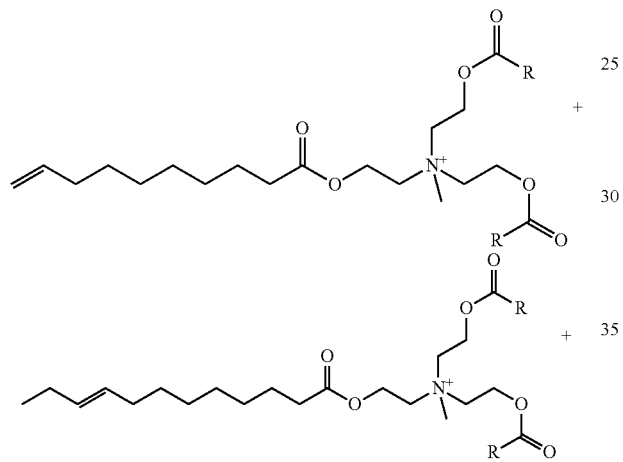

-continued

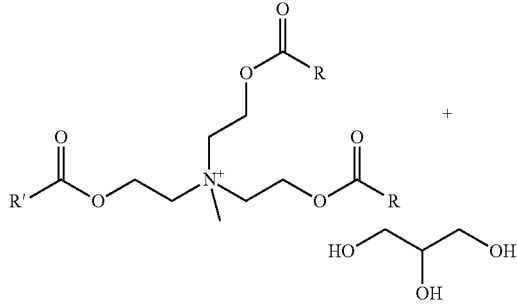

wherein R' is a saturated $C_{16}$ or $C_{18}$ group or an unsaturated $C_{16}$ or $C_{18}$ group; and wherein R is a saturated $C_{10}$ group or a saturated $C_{12}$ to $C_{18}$ group or an unsaturated $C_{10}$ group or an unsaturated $C_{12}$ to $C_{18}$ group;

and (h)

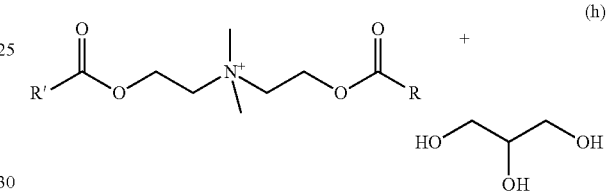

wherein R is a saturated $C_{10}$ group or a saturated $C_{12}$ to $C_{18}$ group or an unsaturated $C_{10}$ group or an unsaturated $C_{12}$ to $C_{18}$ group;

and wherein R' is a saturated Cio group or a saturated $C_{12}$ to $C_{18}$ group or an unsaturated $C_{10}$ group or an unsaturated $C_{12}$ to $C_{18}$ group.

* * * * *